US009416370B2

(12) United States Patent
Smith et al.

(10) Patent No.: US 9,416,370 B2
(45) Date of Patent: Aug. 16, 2016

(54) ALPHAVIRUS REPLICON PARTICLES MATCHED TO PROTEIN ANTIGENS AS IMMUNOLOGICAL ADJUVANTS

(75) Inventors: Jonathan F. Smith, Cary, NC (US); Bolyn Hubby, Cary, NC (US); Laura Copp, Raleigh, NC (US)

(73) Assignee: AlphaVax, Inc., Research Triangle Park, NC (US)

( * ) Notice: Subject to any disclaimer, the term of this patent is extended or adjusted under 35 U.S.C. 154(b) by 1219 days.

(21) Appl. No.: 12/906,992

(22) Filed: Oct. 18, 2010

(65) Prior Publication Data

US 2011/0086062 A1 Apr. 14, 2011

Related U.S. Application Data

(63) Continuation of application No. 11/854,533, filed on Sep. 12, 2007, now abandoned.

(60) Provisional application No. 60/825,394, filed on Sep. 12, 2006.

(51) Int. Cl.
*A61K 39/12* (2006.01)
*C12N 15/86* (2006.01)
*A61K 39/145* (2006.01)
*A61K 39/00* (2006.01)

(52) U.S. Cl.
CPC ................ *C12N 15/86* (2013.01); *A61K 39/12* (2013.01); *A61K 39/145* (2013.01); *A61K 2039/5256* (2013.01); *A61K 2039/70* (2013.01); *C12N 2760/16134* (2013.01); *C12N 2770/36143* (2013.01)

(58) Field of Classification Search
CPC ........... A61K 39/12; A61K 2039/5256; C12N 2760/16134; C12N 2270/36143
See application file for complete search history.

(56) References Cited

U.S. PATENT DOCUMENTS 5,185,440 A 2/1993 Davis et al.
5,505,947 A 4/1996 Johnston et al.
5,643,576 A 7/1997 Johnston et al.
5,789,245 A 8/1998 Dubensky, Jr. et al.
5,792,462 A 8/1998 Johnston et al.
5,814,482 A 9/1998 Dubensky, Jr. et al.
5,843,723 A 12/1998 Dubensky, Jr. et al.
6,008,035 A 12/1999 Johnston et al.
6,015,686 A 1/2000 Dubensky, Jr. et al.
6,015,694 A 1/2000 Dubensky, Jr. et al.
6,156,558 A 12/2000 Johnston et al.
6,190,666 B1 2/2001 Garoff et al.
6,242,259 B1 6/2001 Polo et al.
6,376,236 B1 4/2002 Dubensky, Jr. et al.
7,045,335 B2 5/2006 Smith et al.
7,078,218 B2 7/2006 Smith et al.
2001/0016199 A1 8/2001 Johnston et al.
2002/0015945 A1 2/2002 Polo et al.
2002/0086837 A1 7/2002 Gauldie et al.
2002/0165172 A1 11/2002 Sallberg et al.
2004/0208848 A1 10/2004 Smith et al.
2005/0031592 A1 2/2005 Doolan et al.
2005/0266550 A1 12/2005 Rayner et al.

FOREIGN PATENT DOCUMENTS

WO 92/10578 6/1992
WO 01/12172 2/2001
WO 2004/000872 12/2003
WO 2004/085660 12/2004
WO 2006/085983 8/2006
WO 2007/047749 4/2007

OTHER PUBLICATIONS

Prosecution history for parent application U.S. Appl. No. 11/854,533, filed Sep. 12, 2007 (downloaded May 26, 2011), last document dated Apr. 6, 2010, 49 pp.
International Preliminary Report on Patentability, mailed Mar. 26, 2009, corresponding to International Application No. PCT/US2007/078331, filed Sep. 12, 2007, 7pp.
Written Opinion, mailed Jun. 4, 2008, corresponding to International Application No. PCT/US2007/078331, filed Sep. 12, 2007, 7 pp.
First Office Action, dated Jul. 13, 2009, in European Application No. 07842383.7, a related application, 2 pp.
Response to First Office Action, dated Nov. 6, 2009, in European Application No. 07842383.7, a related application, 8 pp.
Second Office Action, dated Mar. 8, 2011, in European Application No. 07842383.7, a related application, 4 pp.
First Office Action, dated Jul. 5, 2010, in New Zealand Application No. 575901, a related application, 2 pp.
International Search Report, mailed Jun. 4, 2008, corresponding to International Application No. PCT/US2007/078331, filed Sep. 12, 2007, 7 pp.
International Search Report and Written Opinion, mailed Sep. 25, 2008, corresponding to International Application No. PCT/US2007/078314, filed Sep. 12, 2007.
Abaitua et al. (Mar. 1, 2006) "Improving Recombinant MVA Immune Responses: Potentiation of the Immune Responses to HIV-1 with MVA and DNA Vector's Expressing Env and the Cytokines IL-12 and IFN-gamma," Virus Res. 116(1-2):11-20.
Bernard et al. (2000) "Mutations in the E2 Glycoprotein of Venezuelan Equine Encephalitis Virus Confer Heparan Sulfate Interaction, Low Morbidity, and Rapid Clearance from Blood of Mice," Virology 276:93-103.

(Continued)

*Primary Examiner* — Stacy B Chen
(74) *Attorney, Agent, or Firm* — Lathrop & Gage LLP

(57) ABSTRACT

The immune response to an antigen of interest, especially one in purified form, can be significantly enhanced by the simultaneous administration of an alphavirus replicon particle which expresses the same antigen. This allows for the use of significantly smaller quantities of the protein antigen than in conventional immunization strategies, and this new immunization strategy can also eliminate the need for boosting administration of the antigen or it can reduce the number of boosts required for an effective immune response to the antigen.

10 Claims, 7 Drawing Sheets

(56) References Cited

OTHER PUBLICATIONS

Davis et al. (Jan. 2000) "Vaccination of Macaques Against Pathogenic Simian Immunodeficiency Virus with Venezuelan Equine Encephalitis Virus Replicon Particles," J. Virol. 74(1):371-378.
Frolov et al. (Oct. 1996) "Alphavirus-Based Expression Vectors: Strategies and Applications," Proc. Nat. Acad. Sci. USA 93:11371-11377.
Glasgow et al. (Dec. 1991) "Two Mutations in the Envelope Glycoprotein E2 of Semliki Forest Virus Affecting the Maturation and Entry Patterns of the Virus Alter Pathogenicity for Mice," Virology 185(2):741-748.
Goldberg et al. (Nov. 2005) "Comparison of Two Cancer Vaccines Targeting Tyrosinase: Plasmid DNA and Recombinant Alphavirus Replicon Particles," Clin. Cancer Res. 11(22):8114-8121.
Hahn et al. (Apr. 1992) "Infectious Sindbis Virus Transient Expression Vectors for Studying Antigen Processing and Presentation," Proc. Nat. Acad. Sci. USA 89:2679-2683.
Heidner et al. (Dec. 1994) "The Amino-Terminal Residue of Sindbis Virus Glycoprotein E2 Influences Virus Maturation, Specific Infectivity for BHK Cells, and Virulence in Mice," J. Virol. 68(12):8064-8070.
Heise et al. (May 2000) "A Single Amino Acid Change in nsP1 Attenuated Neurovirulence of the Sindbis-Group Alphavirus S.A. AR86," J. Virol. 74(9):4207-4213.
Hill et al. (Apr. 1997) "RNA-RNA Recombination in Sindbis Virus: Roles of the 3' Conserved Motif, Poly(A) Tail, and Nonviral Sequences of Template RNAs in Polymerase Recognition and Template Switching," J. Virol. 71(4):2693-2704.
Johnston et al. (1988) "Selection for Accelerated Penetration in Cell Culture Coselects for Attenuated Mutants of Venezuelan Equine Encephalitis Virus," Virology 162:437-443.
Kamrud et al. (Apr. 10, 2007) "Alphavirus Replicon Approach to Promoterless Analysis of IRES Elements," Virology 360(2):376-387.
Kinney et al. (1989) "The Full-Length Nucleotide Sequences of the Virulent Trinidad Donkey Strain of Venezuelan Equine Encephalitis Virus and Its Attenuated Vaccine Derivative, Strain TC-83," Virology 170:19-30.
Klimstra et al. (Dec. 1999) "Infection of Neonatal Mice with Sindbis Virus Results in a Systemic Inflammatory Response Syndrome," J. Virol. 73(12):10387-10398.
Kunkel, T.A. (Jan. 1985) "Rapid and Efficient Site-Specific Mutagenesis without Phenotypic Selection," Proc. Nat. Acad. Sci. USA 82:488-492.
Lu et al. (2001) "Transmission of Replication-Defective Sindbis Helper Vectors Encoding Capsid and Envelope Proteins," J. Virol. Methods 91(1):59-65.
Olmsted et al. (Jul. 27, 1984) "Sindbis Virus Mutants Selected for Rapid Growth in Cell Culture Display Attenuated Virulence in Animals," Science 225:424-427.
Pedersen et al. (Oct. 1974) "Separation, Isolation, and Immunological Studies of the Structural Proteins of Venezuelan Equine Encephalomyelitis Virus," J. Virol. 14(4):740-744.
Polo et al. (Sep. 1990) "Attenuating Mutations in Glycoproteins E1 and E2 of Sindbis Virus Produce a Highly Attenuated Strain When Combined In Vitro," J. Virol. 64(9):4438-4444.
Pushko et al. (1997) "Replicon-Helper Systems from Attenuated Venezuelan Equine Encephalitis Virus: Expression of Heterologous Genes in Vitro and Immunization Against Heterologous Pathogens in Vivo," Virology 239:389-401.
Rayner et al. (Sep. 1, 2002) "Alphavirus Vectors and Vaccination," Rev. Med. Virol. 12(5):279-296.
Rodriguez-Madoz, Jr. et al. (Apr. 12, 2005) "Semliki Forest Virus Vectors Engineered to Express Higher IL-12 Levels Induce Efficient Elimination of Murine Colon Adenocarcinomas," Mol. Ther. 12(1):153-163.
Rosenberg, S.A. (Mar. 1999) "A New Era for Cancer Immunotherapy Based on the Genes that Encode Cancer Antigens," Immunity 10:281-287.
Schlesinger et al. (1986) "Defective RNAs of Alphaviruses," In; *The Togaviridae and Flaviviridae*, Plenum Publishing Corp., New York, Ch. 6, 149-169.
Smerdou et al. (Feb. 1999) "Two-Helper RNA System for Production of Recombinant Semliki Forest Virus Particles," J. Virol. 73(2):1092-1098.
Smit et al. (Nov. 2001) "PE2 Cleavage Mutants of Sindbis Virus: Correlation Between Viral Infectivity and pH-Dependent Membrane Fusion Activation of the Spike Heterodimer," J. Virol. 75(22):11196-11204.
Thompson et al. (Mar. 7, 2006) "Mucosal and Systemic Adjuvant Activity of Alphavirus Replicon Particles," Proc. Nat. Acad. Sci. USA 103(10):3722-3727.
Weaver et al. (2004) "Venezuelan Equine Encephalitis," Ann. Rev. Entomol. 49:141-174.
White et al. (Apr. 2001) "Role of Alpha/Beta Interferon in Venezuelan Equine Encephalitis Virus Pathogenesis: Effect of an Attenuating Mutation in the 5' Untranslated Region," J. Virol. 75:3706-3718.
Xu et al. (Oct. 10, 2006) "Characterization of Immune responses Elicited in Macaques Immunized Sequentially with Chimeric Vee/SIN Alphavirus Replicon Particles Expressing SIVGag and/or HIVEnv and with Recombinant HIVgp140Env Protein," Aids Res. Human Retroviruses 22(10):1022-1030.
Yu et al. (Dec. 2006) "Enhanced Immunogenicity to Food- and-Mouth Disease Virus in Mice Vaccination with Alphaviral Replicon-Based DNA Vaccine Expressing the Capsid Precursor Polypeptide (P1)," Virus Genes 33:337-344.
Third European Office Action response, dated May 23, 2013, in European Patent Application No. 07842383.7, a related application, 16 pp.
First Australian Office Action response, dated Oct. 24, 2012, in Australian Application No. 2007296489, a related application, 11 pp.
Second Australian Office Action, dated Nov. 19, 2012, in Australian Patent Application No. 2007296489, a related application, 3 pp.
Second Australian Office Action response, dated Apr. 24, 2013, in Australian Application No. 2007296489, a related application, 9 pp.
Australian Patent Office allowance communication, dated Jun. 21, 2013, in Australian Application No. 2007296489, a related application, 4 pp.
Requisition by the Examiner corresponding to Canadian Patent Application No. 2,663,295, dated Oct. 28, 2013.
Zhu et al. (Nov. 2005) "Comparison of Immune Responses to Gonococcal PorB Delivered as Outer Membrane Vesicles, Recombinant Protein, or Venezuelan Equine Encephalitis Virus Replicon Particles," *Infection and Immunity*. 73:7558-7568.
Second European Office Action response, dated Sep. 12, 2011, in European Application No. 07842383.7, a related application, 3 pp.
Third European Office Action, dated Mar. 15, 2013, in European Patent Application No. 07842383.7, a related application, 3 pp.
First New Zealand Office Action response, dated Jul. 25, 2011, in New Zealand Application No. 575901, a related application, 3 pp.
Second New Zealand Office Action, dated Aug. 4, 2011, in New Zealand Patent Application No. 575901, a related application, 2 pp.
Second New Zealand Office Action response, dated Sep. 14, 2011, in New Zealand Application No. 575901, a related application, 3 pp.
Third New Zealand Office Action, dated Oct. 3, 2011, in New Zealand Patent Application No. 575901, a related application, 1 pp.
Third New Zealand Office Action response, dated Dec. 9, 2011, in New Zealand Application No. 575901, a related application, 2 pp.
Fourth New Zealand Office Action response, dated Feb. 27, 2012, in New Zealand Application No. 575901, a related application, 1 pp.

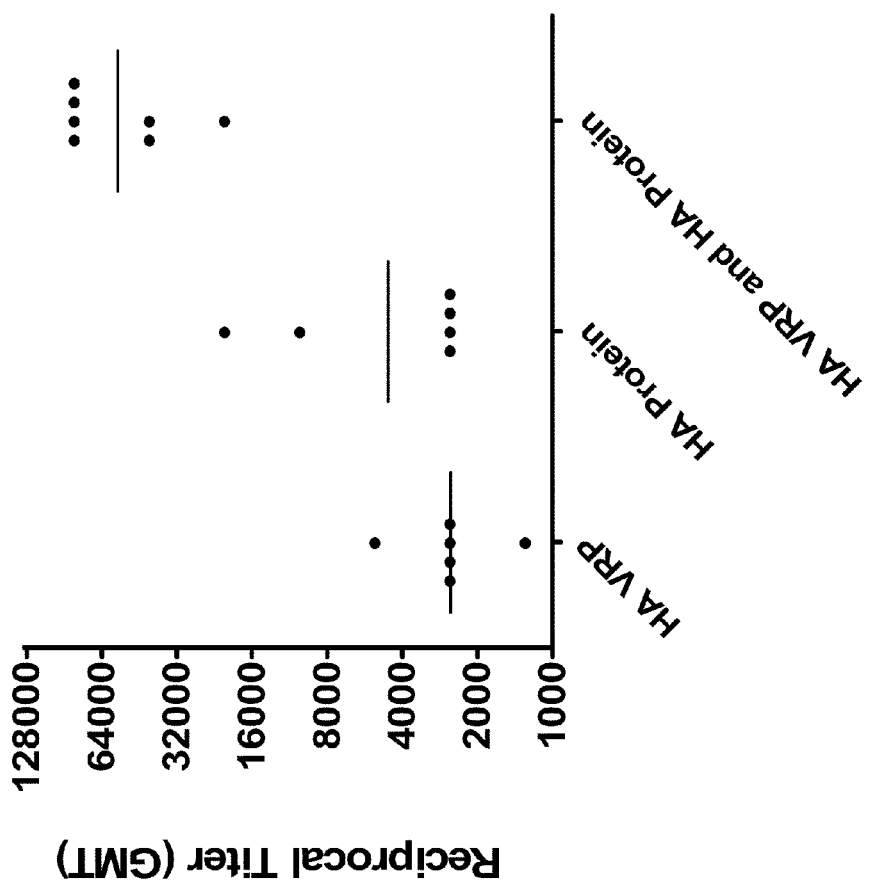

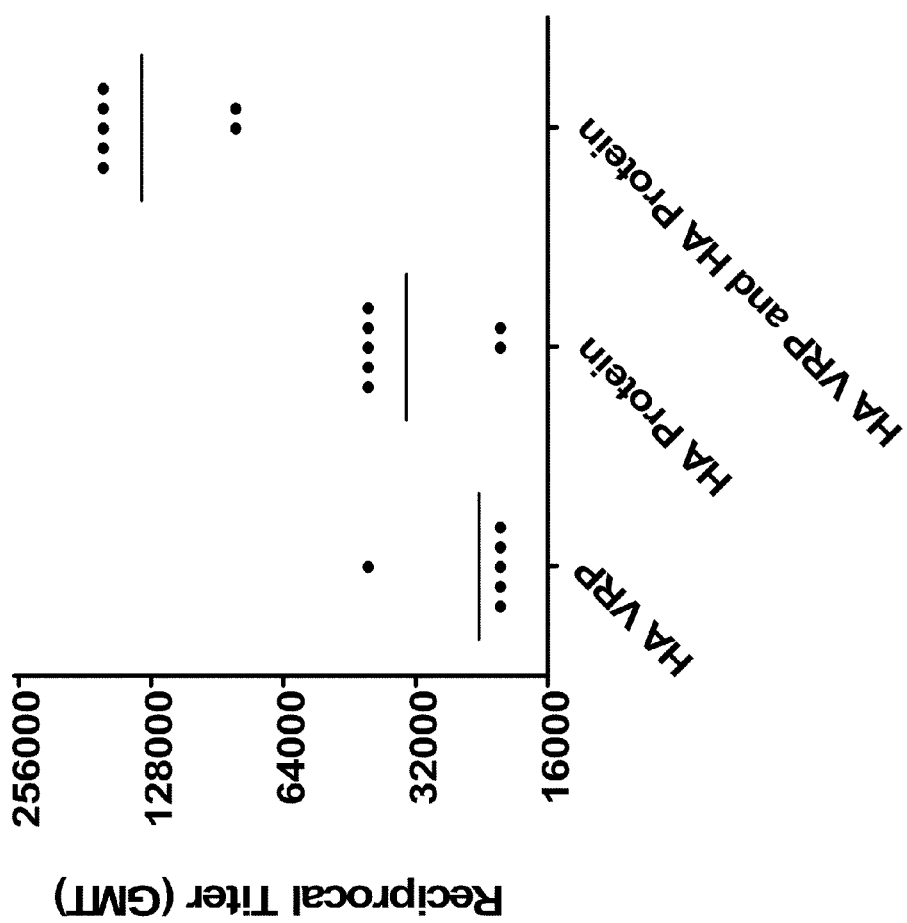

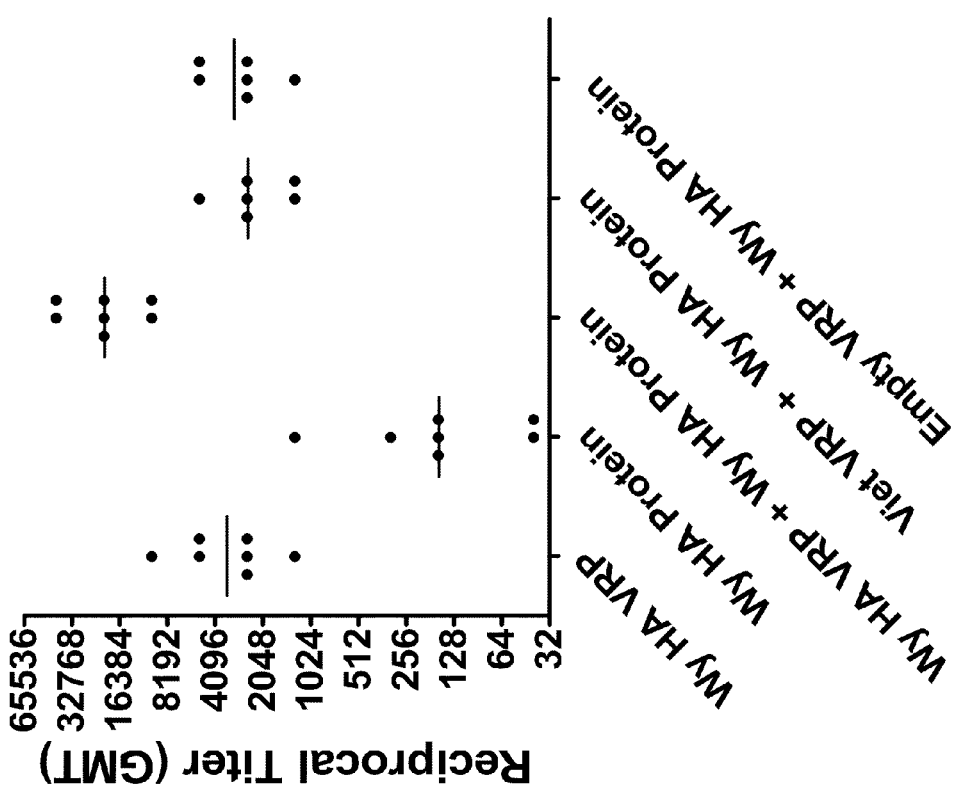

SEQUENCE LISTING

<160> NUMBER OF SEQ ID NOS: 5

<210> SEQ ID NO 1
<211> LENGTH: 27
<212> TYPE: DNA
<213> ORGANISM: Artificial
<220> FEATURE:
<223> OTHER INFORMATION: Synthetic construct: oligonucleotide useful as a primer.

<400> SEQUENCE: 1
ccttaattaa atgaagacta tcattgc                                              27

<210> SEQ ID NO 2
<211> LENGTH: 26
<212> TYPE: DNA
<213> ORGANISM: Artificial
<220> FEATURE:
<223> OTHER INFORMATION: Synthetic construct: oligonucleotide useful as a primer.

<400> SEQUENCE: 2
ttggcgcgcc tcaaatgcaa atgttg                                               26

<210> SEQ ID NO 3
<211> LENGTH: 25
<212> TYPE: DNA
<213> ORGANISM: Artificial
<220> FEATURE:
<223> OTHER INFORMATION: Synthetic construct: oligonucleotide useful as a primer.

<400> SEQUENCE: 3
cgtctagaat gaagactatc attgc                                                25

<210> SEQ ID NO 4
<211> LENGTH: 31
<212> TYPE: DNA
<213> ORGANISM: Artificial
<220> FEATURE:
<223> OTHER INFORMATION: Synthetic construct: oligonucleotide useful as a primer.

<400> SEQUENCE: 4
taaaatctag attaaatgca aatgttgcac c                                         31

<210> SEQ ID NO 5
<211> LENGTH: 1701
<212> TYPE: DNA
<213> ORGANISM: Artificial
<220> FEATURE:
<223> OTHER INFORMATION: Synthetic construct: A/Wyoming/3/2003 Coding Sequence Generated from Viral RNA by rtPCR

<400> SEQUENCE: 5
atgaagacta tcattgcttt aagctacatt ctatgcctgg ttttctctca aaagcttccc     60
ggaaatgaca acagcacggc aacgctgtgc cttgggcacc atgcagtacc aaacggaacg    120
atagtgaaaa caatcacgaa tgaccaaatt gaagttacta atgctactga gctggttcag    180
agttcctcaa caggtggaat atgcgacagt cctcatcaga tccttgatgg agaaaactgc    240
acactaatag atgctctatt gggagaccct cagtgtgatg gcttccaaaa taagaaatgg    300 gaccttttg ttgagcgcag caaagcctac agcaactgtt accttatga tgtgccggat    360 tatgcctccc ttaggtcact agttgcctca tccggcacac tggagtttaa caatgaaagc    420

```
-continued ttcaattggg ctggagtcac tcagaatgga acaagctctg cttgcaaaag gagatctaat    480
aaaagtttct ttagtagatt gaattggttg acccacttaa aatacaaata cccagcattg    540
aacgtgacta tgccaaacaa tgaaaaattt gacaaattgt acatttgggg ggttcaccac    600
ccggttacgg acagtgacca aatcagccta tatgctcaag catcaggaag aatcacagtc    660
tctaccaaaa gaagccaaca aactgtaatc ccgaatatcg gatatagacc cagggtaagg    720
gatatctcca gcagaataag catctattgg acaatagtaa aaccgggaga catacttttg    780
attaacagca caggaaatct aattgctcct cggggttact tcaaaatacg aagtgggaaa    840
agctcaataa tgagatcaga tgcacccatt ggcaaatgca attctgaatg catcactcca    900
aatggaagca ttcccaatga caaccatttt caaaatgtaa acaggatcac atatgggcc     960 tgtcccagat atgttaagca aaacactctg aaattggcaa cagggatgcg aaatgtacca   1020
gagaaacaaa ctagaggcat atttggcgca atcgcgggtt tcatagaaaa tggttgggag   1080
ggaatggtgg acggttggta cggtttcagg catcaaaatt ctgagggcac aggacaagca   1140
gcagatctca aaagcactca agcagcaatc aaccaaatca atgggaaact gaataggtta   1200
atcgggaaaa caaacgagaa attccatcag attgaaaaag aattctcaga agtagaaggg   1260
agaattcagg acctcgagaa atatgttgag gacactaaaa tagatctctg gtcatacaac   1320
gcggagcttc ttgttgccct ggaaaaccaa catacaattg atctaactga ctcagaaatg   1380
aacaaactgt ttgaaagacc aaagaagcaa ctgagggaaa atgctgagga tatgggcaat   1440
ggttgtttca aaatatacca caaatgtgac aatgcctgca tagagtcaat cagaaatgga   1500
acttatgacc atgatgtata cagagatgaa gcattaaaca accggttcca gatcaaaggt   1560
gttgagctga agtcaggata caaagattgg atcctatgga tttcctttgc catatcatgt   1620
tttttgcttt gtgttgcttt gttggggttc atcatgtggg cctgccaaaa aggcaacatt   1680
aggtgcaaca tttgcattta a                                              1701
```

ALPHAVIRUS REPLICON PARTICLES MATCHED TO PROTEIN ANTIGENS AS IMMUNOLOGICAL ADJUVANTS

CROSS-REFERENCE TO RELATED APPLICATIONS

This application is a Continuation of U.S. application Ser. No. 11/854,533, filed Sep. 12, 2007, now abandoned, which application claims benefit of U.S. Provisional Application 60/825,395, filed Sep. 12, 2006, which application is incorporated by reference herein to the extent there is no inconsistency with the present disclosure.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The present invention relates to recombinant DNA technology, and in particular to introducing foreign nucleic acid(s) in a eukaryotic cell, and more particularly to methods for producing immunogenic compositions comprising infective virus particles or virus-like particles in high yields, especially particles useful in immunotherapies, vaccines and/or immunogenic compositions. In particular, the present application discloses highly purified alphavirus replicon particle (ARP) preparations, especially those expressing an antigen of interest suitable for use in human and veterinary medicine and for enhancing the immune system's response to a concurrently administered antigen.

The Alphavirus genus includes a variety of viruses, all of which are members of the Togaviridae family. The alphaviruses include Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus. The viral genome is a single-stranded, messenger-sense RNA, modified at the 5'-end with a methylated cap and at the 3'-end with a variable-length poly (A) tract. Structural subunits containing a single viral protein, capsid, associate with the RNA genome in an icoshedral nucleocapsid. In the virion, the capsid is surrounded by a lipid envelope covered with a regular array of transmembrane protein spikes, each of which consists of a heterodimeric complex of two glycoproteins, E1 and E2. See Pedersen et al. 1974. J. Virol. 14:40. The Sindbis and Semliki Forest viruses are considered the prototypical alphaviruses and have been studied extensively. See Schlesinger, The Togaviridae and Flaviviridae, Plenum Publishing Corp., New York (1986). The VEE virus has been studied extensively, see, e.g., U.S. Pat. No. 5,185, 440.

The studies of these viruses have led to the development of techniques for vaccinating against the alphavirus diseases and against other diseases through the use of alphavirus vectors for the introduction of foreign genes. See U.S. Pat. No. 5,185, 440 to Davis et al., and PCT Publication WO 92/10578. The use of alphavirus vectors to direct the expression of foreign genes in eukaryotes has become a topic of increasing interest. It is well known that live, attenuated viral vaccines are among the most successful means of controlling viral or other disease. However, for some virus pathogens, immunization with a live virus strain may be either impractical or unsafe. One alternative strategy is the insertion of sequences encoding immunizing antigens of such agents into a live, replicating strain of another virus. One such system utilizing a live VEE vector is described in U.S. Pat. Nos. 5,505,947 and 5,643,576 to Johnston et al. Another such system is described by Hahn et al., *Proc. Natl. Acad. Sci. USA* 89:2679-2683 (1992), wherein Sindbis virus constructs express a truncated form of the influenza hemagglutinin protein. Another system is the alphavirus replicon system, as described in U.S. Pat. No. 6,190,666 to Garoff et al., U.S. Pat. Nos. 5,792,462 and 6,156,558 to Johnston et al., U.S. Pat. Nos. 5,814,482, 5,843, 723, 5,789,245, 6,015,694, 6,105,686 and 6,376,236 to Dubensky et al; U.S. Published Application No. 2002-0015945 A1 (Polo et al.), U.S. Published Application No. 2001-0016199 (Johnston et al.), Frolov et al. (1996) *Proc. Natl. Acad. Sci. USA* 93:11371-11377 and Pushko et al. (1997) *Virology* 239:389-401.

There remains a need in the art for methods which allow the production of a more effective immune response to an administered immunogenic composition, especially an immunogenic composition comprising at least one protein antigen and one or more types of alphavirus replicon particles expressing the same protein antigen(s), especially a composition comprising less antigen than in a conventional vaccine composition of such antigen, especially where a protective or therapeutic immune response is sought, such that there is less severe disease, reduced risk of disease or no disease in response to the relevant pathogen, cancer or metabolic disorder.

BRIEF SUMMARY

Provided are methods of enhancing the immune response in a subject in which there is co-administered an immunogenic composition comprising an immunogenic protein and alphavirus replicon particles expressing the same, or similar, immunogenic protein. Advantageously, the particles are administered simultaneously with or promptly after the administration of the immunogenic protein, and desirably the particles and the immunogenic protein are administered simultaneously and at the same location. In these methods, the route of administration can be subcutaneous, intramuscular, intranasal, intravenous, intraperitoneal or mucosal (genital, nasal, respiratory, rectal or gastrointestinal). The dose of alphavirus replicon particles can be at least $1\times10^2$, $1\times10^3$, $1\times10^4$, $1\times10^5$ or $1\times10^6$ infectious units (IU) per ml, as measured by assay on alphavirus permissive cultured cells, and reflects the range of dose-sparing that may be accomplished by practicing the methods and compositions of this invention. Alternatively, higher doses can be used to achieve an enhancement of an immune response, especially in diseases where it is more difficult to raise a robust immune response, e.g. in cancer where tolerance to the self-antigen must be broken to achieve the immune response. In such situations, the dose of alphavirus replicon particles used may be the same as that used in the absence of the immunogenic protein.

Typically, a dose of alphavirus replicon particles alone that is effective is at least $1 \times 10^6$, and may range to $1 \times 10^7$, $1 \times 10^8$, and $1 \times 10^9$, IU per ml.

In the methods described herein, the alphavirus replicon particles can be derived from Venezuelan Equine Encephalitis (VEE) virus, and are preferably derived from an attenuated strain of VEE, e.g. TC-83 (see Smith et al., U.S. Patent Publication 2005-0266550, incorporated herein by reference).

The present application includes a method of sparing the dose of an immunogenic protein required to provide effective immunization of a subject comprising co-administering alphavirus replicon particles capable of expressing the immunogenic protein together with the immunogenic protein. The dose of alphavirus replicon particles is preferably at least $1 \times 10^2$, $1 \times 10^3$, $1 \times 10^4$, $1 \times 10^5$, or $1 \times 10^6$ infectious units (IU) per ml, as measured by assay on alphavirus permissive cultured cells. In the present methods, the dose of immunogenic protein used is at least two-fold, three-, or five- or ten-fold less than the dose of said immunogenic protein required to provide effective immunization alone (that is, without an ARP preparation for expressing the same, or similar, protein). In certain embodiments, the dose of immunogenic protein used is at least 50- or 100-fold less than the dose of said immunogenic protein required to provide effective immunization alone.

In another aspect, there is a boost-sparing composition, wherein the number of doses of a vaccine or immunotherapeutic composition required to provide effective immunization of a subject is reduced by administering alphavirus replicon particles capable of expressing the immunogenic protein together with the immunogenic protein.

Also provided by the present application are vaccine compositions comprising (a) purified protein(s) and (b) alphavirus replicon particles capable of expressing the same, or similar, protein(s). Advantageously the alphavirus from which the alphavirus replicon particles are derived is Venezuelan Equine Encephalitis (VEE) virus, and such particles may be referred to as "VRPs" herein. The compositions can further comprise a pharmaceutically acceptable carrier or excipient.

In the methods and compositions provided herein, the immunogenic protein can be at least one influenza virus immunogenic protein, especially a hemagglutinin protein, or other protein to which a human produces a protective immune response after administration of an immunogenic composition comprising same. The immunogenic protein can be a full-length protein or an immunogenic fragment or epitope thereof. Particularly preferred for influenza-derived immunogenic compositions are those which comprise more than one antigenic type, such as the trivalent inactivated influenza vaccine preparations or mixed cocktails of recombinantly produced protein. Other immunogenic proteins can be derived from other viral pathogens, such as measles, mumps, rubella, rubeola, vaccinia, herpesviruses, among others. For prophylaxis for bacterial diseases, the immunogenic protein can be (attenuated) anthrax toxins and antigens from *Bacillus anthracis*, antigens from *Yersinia pestis*, inactive diphteria toxin from *Corynebacterium diphtheriae*, inactive toxin from *Clostridium botulinum, Chlamydia* species, *Mycobacterium tuberculosis*, and a host of others known to the art. Protein, glycoprotein, lipoprotein, toxin, attenuated toxin, inactivated toxin, virus, cancer cell antigens, bacterial proteins or portion(s) thereof, inactivated toxins or other bacterial proteins, fungal proteins or portion(s) thereof, attenuated fungus, inactivated fungus, parasite or proteins or portion(s) thereof, protozoan proteins or portion(s) thereof, and the expression product of a minigene encoding a series of epitopes of interest, for example from different influenza virus serotypes, can all be incorporated in the methods and compositions. In addition, neoplastic cell antigens can be incorporated into the dose sparing vaccine strategies for therapeutic or prophylactic immunizations. Alternatively, the immunogenic protein or polypeptide can be any tumor or cancer cell antigen. The tumor or cancer antigen can be one expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281) and include, but are not limited to, MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl(asparaginyl)β-hydroxylase (HAAH), and EphA2 (an epithelial cell tyrosine kinase, see International Patent Publication No. WO 01/12172).

BRIEF DESCRIPTION OF THE DRAWINGS

FIG. 1 shows the synergistic enhancement of humoral responses upon co-delivery of matching protein and VRP-based vaccines. Groups of 6 Balb/c mice were immunized intraperitoneally with 15 μg of baculovirus-expressed HA protein, $1 \times 10^7$ IU of HA VRP or the two combined and boosted at 3 weeks post-priming. Antibody titers were measured as reciprocal ELISA titers and are indicated in the figure: FIG. 1A: Titers at 3 weeks post-priming, just prior to the boosting inoculation; FIG. 1B: Titers measured at 1 week post-boost. The geometric mean titers are shown as the horizontal bar.

FIG. 2 shows synergistic enhancement of humoral responses upon co-delivery of a low dose of matching protein and VRP-based vaccines. Groups of 6 Balb/c mice were immunized subcutaneously with 100 ng of HA protein, $1 \times 10^7$ IU of HA VRP or the two combined and boosted at 3 weeks post-priming. Antibody titers were measured as reciprocal ELISA titers and are indicated in the figure: FIG. 2A: Titers at 3 weeks post-priming, just prior to the boosting inoculation.

DETAILED DESCRIPTION

Figure 2B:
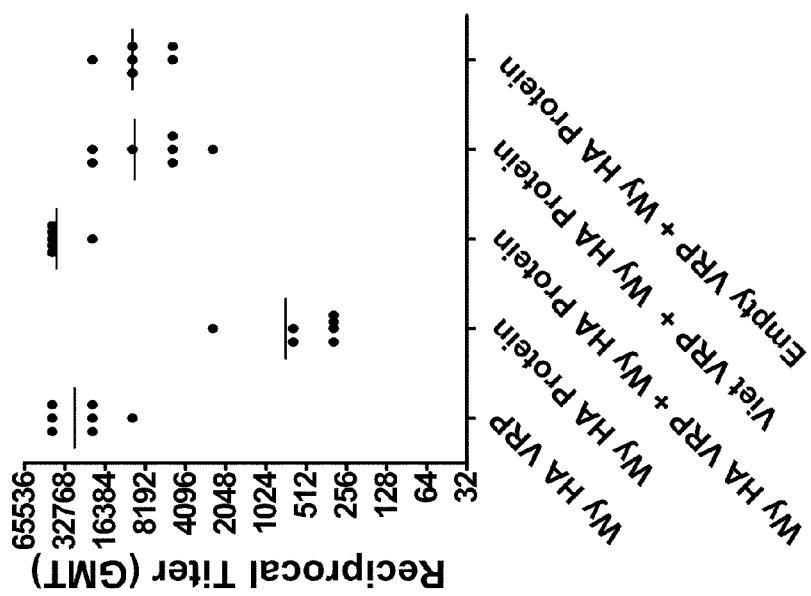
FIG. 2B: Titers measured at 1 week post-boost. The geometric mean titers are shown as the horizontal bar. "Wy HA" is the H3 HA from the Wyoming influenza strain; "Viet VRP" are VRP expressing the H5 HA gene from the Vietnam strain of avian influenza. "Empty" VRP are VRP which do not encode an antigen.

There is a need in the art for cost-effective, potent, dose-sparing and or boost-sparing vaccine adjuvants, especially with respect to cancer, toxin and influenza vaccines, as well as vaccines for other diseases. The present application provides an RNA replicon vector system, derived from an alphavirus that is preferably attenuated, to produce single-cycle, propagation-defective alphavirus-like replicon particle (ARP) adjuvants containing self-replicating RNA (replicon) expressing an antigen of interest to be administered together with the same antigen in a pharmaceutically acceptable carrier, and potentially with a conventional immunological adjuvant or an alphavirus replicon particle expressing an immunostimulatory protein, for example, interleukin-12 (IL-12). When inoculated into animals, these ARP adjuvants significantly enhance the humoral and cellular immune responses to immunogenic materials, such as subunit-based vaccines, proteins or other antigens of interest. It is particularly important to generate a rapid and strong response to a pathogen, for example, a seasonal or pandemic influenza virus.

A benefit of the present methods and compositions is that they are, at least in part, "dose-sparing", meaning the amount of material in a given dose can be reduced and still achieve effective immunization, or as "boost-sparing", meaning the number of injections or inoculations needed to achieve effective immunization or immune response can be reduced. As an example, many vaccines require 3 injections, spaced over 6 to 12 months. The compositions claimed herein may reduce the number of injections to 2, or in the case of a single boosting vaccination such as the annual influenza vaccine booster, to one injection. Alternatively, the present compositions can be used at higher doses and with regular prime-boost regimens to provide a more robust immunization (immune response).

The present methods and compositions relate to a combination of a protein antigen and an ARP expressing that protein antigen, i.e. "matched" (the same) components. It is anticipated that either the "match" may be exact, or that they may be closely related antigens. For example, the H3 serotype of the hemagglutinin protein from the influenza virus has many variants, such as Wyoming and Wisconsin variants, which share several epitopes. One embodiment is a composition comprising H3 Wyoming HA protein combined with ARP expressing the H3 Wyoming HA protein, and a second embodiment comprises H3 Wisconsin HA protein combined with ARP expressing the H3 Wyoming HA protein. The immunogenic composition administered to a subject comprises the protein antigen(s) of interest, as well as ARPs which express the same, i.e. matched, antigen(s). Alternatively, separate compositions comprising the antigen and the ARPs can be administered to achieve the same beneficial result.

The protein antigen can be at least one protein extracted from a microorganism, virus, parasite, or tumor or tumor cell or such a protein produced recombinantly in eukaryotic or prokaryotic expression systems. In preferred embodiments, the protein is presented with some or all of its native conformation intact to assure elicitation of neutralizing antibodies to the protein. The protein antigen can be one or more epitopes which have been synthesized, purified from protein digests, or produced recombinantly in an expression system that allows presentation of multiple epitopes, e.g. a "mini-gene".

One specific aspect the present methods and compositions is the magnitude of the enhancement of humoral, or antibody, responses when ARP expressing an antigen are co-administered with a protein preparation of a "matched" (the same) antigen. This magnitude can be anywhere from 2 fold to over 100-fold; 5-fold and 10-fold enhancement is typical. Such an enhancement is surprising, given the transient nature of expression and the localized functioning of ARPs, and it is useful in improving vaccine effectiveness and providing high levels of antibodies for collection to use in research, diagnostic and therapeutic applications.

In the present context, the ARPs which express the protein antigen of interest can be viewed as serving as adjuvant ARPs to the protein antigen, although it is well-established that antigen-expressing ARPs can induce an immune response when administered alone to a subject. The adjuvant ARPs are tested in a nonhuman primate model. In addition to optimization, these studies include monitoring for toxicity and characterization of dose-sparing effects due to VRP adjuvants. For this purpose, existing influenza vaccines such as the trivalent influenza vaccine (TIV) or an inactivated H5NI Indonesia, H5N1 Vietnam or other influenza strain can be used, and functional immune responses to Influenza A strains or other relevant strains are measured.

Influenza rapidly spreads around the world in seasonal epidemics, killing potentially millions of people in pandemic years and hundreds of thousands in nonpandemic years. It creates health care costs with 200,000 hospitalizations in the US alone and further costs associated with lost productivity. The 20th century saw three influenza pandemics each following an antigenic shift in the hemagglutinin (HA) gene, which killed millions of people (not limited to elderly) all over the world. The world's current major influenza pandemic threat is H5, for which there is no current immunity in the population.

Vaccination remains the most efficient and cost-effective method to protect the public against influenza. Although novel approaches are being explored, vaccines produced using traditional egg-grown killed influenza virus continue to be used. Nevertheless, there are serious shortcomings in the technology, including dependency on eggs, unpredictable antigenicity and hence dose requirement, risk of producing vaccines against wrong type of Influenza virus, and risks of insufficient amounts of vaccine doses to protect the public, requiring heavy prioritization for health care officials. Illustrating the need for improvements, 5-20% of Americans contract influenza every year, causing on average 36,000 deaths during the 1990s, in spite of yearly vaccination efforts. According to CDC 218.1 million people in the US will be included in the recommended target groups for vaccination, including 91.2 million with high risk status. The self-reported influenza coverage monitored by the US National Health Interview Survey (NHIS) shows little increase over the past 10 years and being as low as 24% and 46% for persons with a high-risk status in the age groups 18-49 and 50-65, respectively, and only 40% among health care workers. A higher vaccine coverage would require the manufacture of several times higher numbers of doses than today's capacity can deliver. This situation is even more pressing for a potential pandemic flu where the projection is that a stronger dose or multiple doses will be required, given that they are administered to immunologically naïve persons, which is normally not the case for seasonal influenza vaccinations. Similar considerations apply to protecting against other infectious agents and potential bioterrorist or biowarfare agents.

The goal to achieve a population-wide protection against both seasonal and pandemic flu would benefit significantly from a technology that could reduce the amount of antigen per dose, the number of required inoculations (esp. in the case of a pandemic influenza vaccine), and/or if today's vaccines could be elevated to induce a broader immune response. While cellular (CTL) responses may have limited use for protection against infection per se, the literature suggests that CTL responses may have a significant role in clearance of influenza infection and in protecting against influenza mortality. Similar considerations apply to other health risks, including but not limited to those associated with bacterial, viral, fungal and other pathogens and parasites, as well as cancers. Protein antigens can be produced recombinantly for use in immunogenic compositions together with ARP expressing the same antigens; administration of such compositions provides superior immune response to that obtained with conventional immunogenic compositions, with reduction in the amount of protein needed, directly or indirectly through the need for fewer administrations per person (or animal) in whom the immune response is sought.

Recent data indicate that both humoral and cellular responses to a target antigen can be enhanced by co-immunization with ARPs expressing immune stimulatory molecules (IS), for example interleukin-12. Pairing this strategy with the matched antigen/ARP strategy could lead to further dose-sparing and/or boost-sparing opportunities insofar as equivalent immune responses can be generated with significantly lower doses or a lower number of inoculations for effective vaccination. This strategy may find particular application in cancer immunotherapy, where it is expected that multiple vaccinations will be required to achieve the optimal response in the subject. This present methods and compositions should minimize the number of treatments that a subject will need to achieve that optimum.

We have demonstrated that vaccinating with a combination of VRP expressing A/Wyoming HA and A/Wyoming HA recombinant protein results in anti-HA antibody responses that are significantly higher than the responses achieved with either the VRP or the recombinant protein alone (FIGS. 1 and 2). A single injection of combined vaccine induced this potent synergistic effect which was attained using only 100 ng of recombinant protein. The dose sparing potential of this vaccine approach on seasonal and pandemic influenza vaccines are evaluated in mice. It is understood that this same strategy of matched antigen protein of interest and antigen protein expressed from a simultaneously administered alphavirus replicon particle preparation which expresses the same antigen is applicable to other protein antigens besides the specifically exemplified hemagglutinin from influenza virus. Other applications include, without limitation, protein antigens from tumor tissues and/or cancer cells, pathogens and parasites, including bacteria including but not limited to *Vibrio cholerae, Shigella dysenteriae, Salmonellae, Yersinia pestis, Yersinia pseudotuberculosis, Streptococcus, Corynebacterium diphtheriae, Staphylococcus, Clostridium perfringens, Clostridium tetani, Clostridium botulinum, Chlamydia species, Mycobacterium tuberculosis*, fungi including but not limited to *Candida, Aspergillus*, protozooans including but not limited to *Giardia*, Amoebae, trypanosomes, *Plasmodium falciparium* and others, *Toxoplasma gondii, Cryptosporidium, Cryptococcus*, and others such as plant, animal, dinoflagellate, algal or bacterial toxins. Alternatively, the immunogenic protein or polypeptide can be any tumor or cancer cell antigen. The tumor or cancer antigen can be one expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281) and include, but are not limited to, MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl(asparaginyl)β-hydroxylase (HAAH), and EphA2 (an epithelial cell tyrosine kinase, see International Patent Publication No. WO 01/12172).

It has been previously observed that ARP have the ability to trigger innate immune pathways irrespectively of the expressed transgenes. Using IFNα/β knock-out mice, it was shown that the potency in eliciting T cell responses was dependent on type I IFN signaling. Another group showed that type I IFN was not required for enhancing the humoral responses. Co-administration of recombinant protein together with ARP expressing an irrelevant transgene, or ARP expressing no transgene at all ("empty VRP", see Thompsom et al. 2006. PNAS 103:3722-3727) resulted in stronger humoral responses to the recombinant protein present in the inoculum. In addition, mucosal humoral responses were enhanced as well. While type I IFN is not required for antigen-expressing ARP potency, these researchers demonstrated that this signaling pathway was required for the ability of empty VRP to enhance humoral responses. Interestingly, cellular responses were not found to be enhanced by co-administration of empty ARP.

Combining ARPs with Protein Immunogens

The procedures used for making VRP used in these studies is based on a two helper system, as described in detail in U.S. Pat. No. 7,078,218. Briefly, capped replicon RNAs were in vitro transcribed using a T7 RiboMax kit (Promega, Madison Wis.) following the manufacturer's instructions, supplemented with 7.5 mM CAP analog (Promega), from a linearized replicon plasmid encoding the antigen (e.g. HA) expressed from a regulatory cassette containing an alphavirus 26S promoter, a spacer (383 nucleotides) and the EV71 IRES. This construct is described in detail in Kamrud et al in Virology 360(2):376-387, 10 Apr. 2007). Uncapped helper plasmids for capsid and glycoprotein were similarly in vitro transcribed. These RNAs were then purified using RNEasy purification columns (Qiagen, Valencia, Calif.) following the manufacturer's instructions. Vero cells (1×108 cells) suspended in PBS were combined with 30 µg of replicon RNA, 30 µg helper RNA, and 60 µg glycoprotein helper RNA in 0.4 cm electroporation cuvettes and were electroporated using a BIO-RAD Gene Pulser (BIO-RAD). The cells and RNA were pulsed four times with the electroporator set at 580 V and 25 µF. Electroporated cell suspensions were seeded into individual roller bottles containing 150 ml of OptiPro medium (Invitrogen) supplemented with antibiotics and incubated at 37° C. in 5% CO2 for 16-24 h. VRP were harvested and stored in aliquots at −80 C. Titers of the VRP were determined by immunofluorescence assay (IFA) using goat anti-VEE nsP2 specific polyclonal antiserum as the primary antibody and donkey anti-goat Alexa Fluor 488 (Invitrogen, Carlsbad, Calif.) as the secondary antibody on methanol fixed cells using a Nikon Eclipse TE300 fluorescence microscope.

Mice were immunized intraperitoneally with (a) recombinant influenza A/Wyoming hemagglutinin (HA) protein, (b) VRP expressing the same HA, or (c) with a cocktail consisting of both HA protein and VRP expressing the matched HA. Surprisingly, ELISA titration of the HA-specific Ig levels (FIG. 2) indicated that mixing the two vaccine compositions had a synergistic effect. In fact, a single immunization with the combined vaccine elicited stronger humoral responses than two doses of the individual components.

Figure 3:
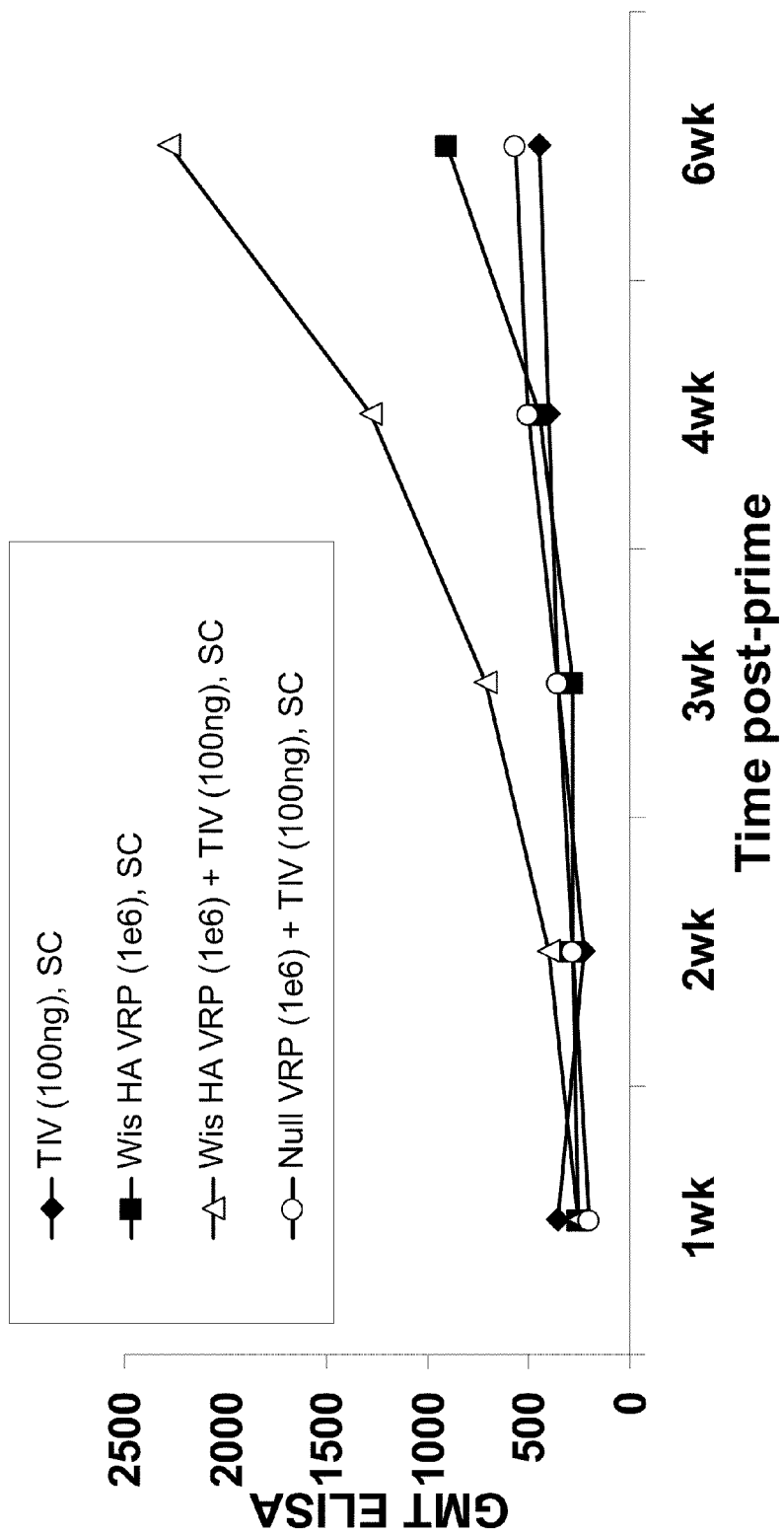
FIG. 3 shows the kinetics of the humoral response after a single dose of the indicated vaccine preparations. Seven (7) mice per group were immunized subcutaneously with a single dose of the vaccine preparation/dose indicated. Humoral responses were measured by an ELISA assay using the H3 Wyoming protein, which cross-reacts with the HA/Wisconsin protein. Differences between the "Wisconsin HA VRP+TIV (100 ng)" data points at 4 and 6 weeks after immunization and the other immunizations are statistically significant.

Similar synergistic humoral responses were observed when mice were immunized subcutaneously with a lower dose (100 ng) of recombinant influenza/Wyoming HA in combination with matched HA VRP (FIG. 3). The results demonstrate that even a much smaller dose (100 ng instead of 15 µg) can be used to trigger very strong responses if co-administered with HA VRP. The proteins had to be matched however, as VRP expressing HA from influenza A/Vietnam (which is of H5 serotype as opposed to H3) failed to elicit HAWyoming-specific antibody titers at the same elevated levels as when matched antigens were used. In fact, the non-matched VRP only had the same adjuvanting activity as empty VRP, which was much weaker than the matched vaccine.

Evaluation of the Boost Sparing Potential of HA VRP Vaccines in Combination with Various Doses of Inactivated Influenza Vaccines For the purpose of studying the matched protein/VRP vaccine approach using a strain relevant for the current seasonal flu vaccine, the HA gene from A/Wisconsin/67/2005 was cloned into the VEE replicon vector. The boost sparing activity of $5 \times 10^6$ IU of this VRP ($HA_{Wis}$ VRP with a low dose of trivalent influenza vaccine (TIV) in BALB/c mice was evaluated. Mice were immunized once subcutaneously or intramuscularly and humoral responses were determined for six weeks following immunization (HI titers, using an assay based on MDCK cell-grown influenza/Wisconsin virus). ELISA titers using recombinant HA as antigen are also determined, and responses beyond six weeks are also monitored. Using a single immunization mimics how a seasonal influenza vaccine would typically be administered, and monitoring the response at longer time points after the single immunization reflects the need to maintain antibody titers throughout the influenza exposure season.

In the case of TIV, which consists of multiple proteins, sera can be analyzed for their specific antibody levels against not only the matched HA but against the two other components $HA_{New\ Caledonia/20/99}$, and $HA_{B/Malaysia/2004}$. The purpose of the latter titration experiment is to determine if the $HA_{Wisconsin}$ VRP has a positive or negative immunomodulary role on the other proteins in the inoculum.

To demonstrate that the synergistic effect on immunogenicity of matched protein/VRP vaccines extends to potentially pandemic strains of influenza, a murine immunogenicity study is performed with VRP expressing the H5 HA gene from A/Indonesia/5/05 in combination with the corresponding inactivated vaccine or with recombinant A/Indonesia/5/05 protein available from Protein Sciences, Inc. (Meriden, Conn.). Various doses of inactivated vaccine or recombinant protein (e.g. 1, 3, 10, 30, 100, 300, or 1000 ng) are studied in combination with varying doses of H5 HA expressing VRPs (e.g. 5e6, 1e7). The A/Indonesia/5/05 HA gene was cloned into the VEE-based replicon to generate VRPs. The A/Indonesia/5/05 6:2 reassortant virus with 6 internal genes from PR8 and HA/NA originating from A/Indonesia/5/05, referred to as Ind05/PR8-RG2 for brevity, is used to develop an internal HI assay.

Figure 5:
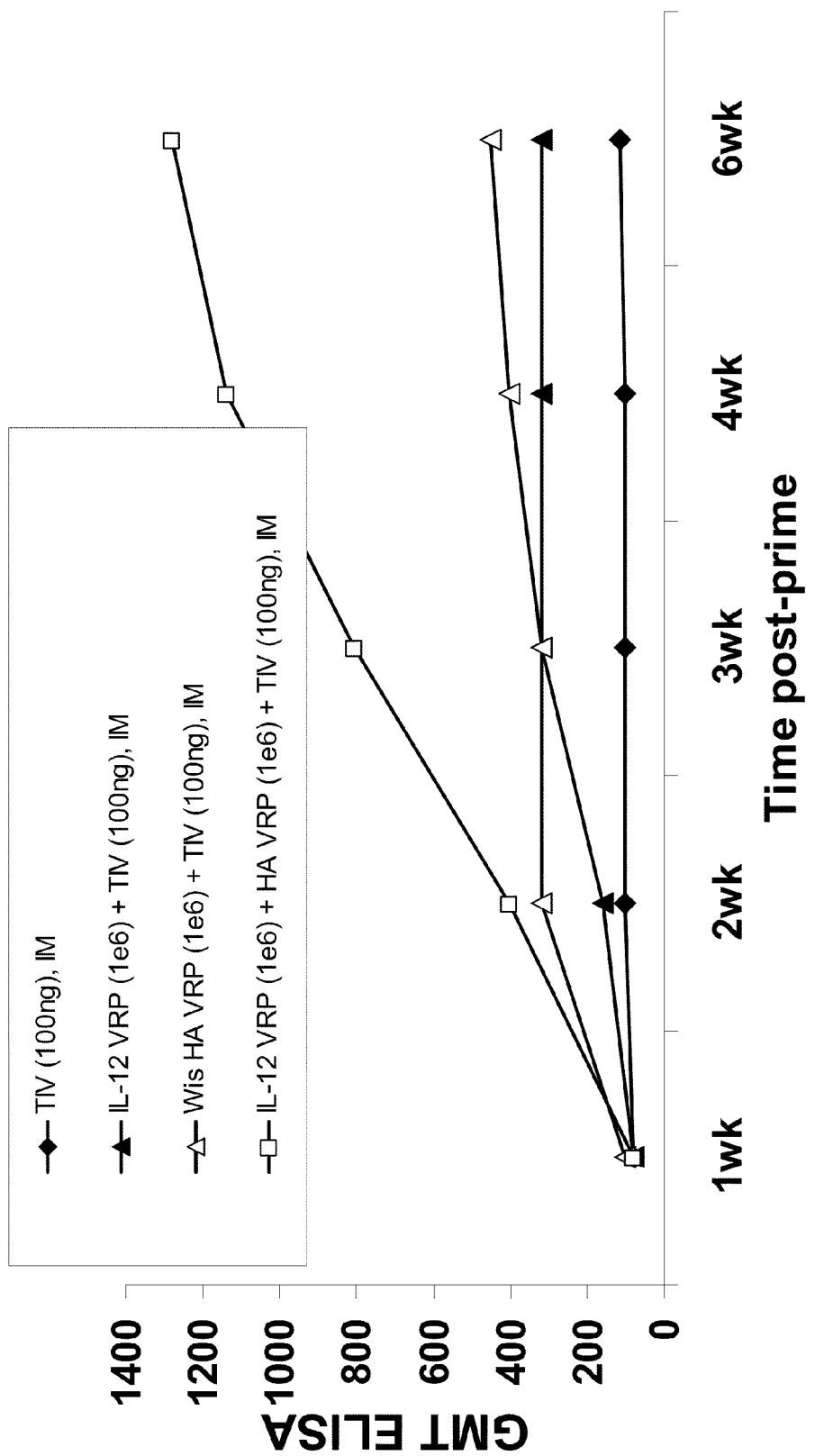
FIG. 5 shows the results of a study in which the matched VRP/antigen vaccination was further enhanced by the co-administration of VRP expressing the cytokine IL-12. Mice were immunized intramuscularly with a single dose of the vaccine preparation/dose indicated, and humoral responses were measured as in FIG. 4.

Determining the optimal doses of matched HA VRP for generating synergistic effects in the immune response to varying doses of inactivated influenza vaccines To determine the optimal dose of matched HA VRP for generating synergistic immune effects, varying doses of inactivated vaccine (TIV) were tested in combination with a range of matched HA VRP doses, as outlined below. In one experiment, BALB/c mice were vaccinated with the specific combinations shown in FIG. 5. Humoral immune responses were monitored as described above. The results show that at a range of low doses of TIV (1, 10 and 100 ng), the immunogenic response is enhanced with the addition of 1e5 matched HA VRP over the response to either TIV or HA VRP alone.

Generation of Alphavirus Replicon Constructs Containing the A/Wyoming/3/2003

HA (Wy HA) Gene

The HA gene from A/Wyoming/3/2003 was amplified by rtPCR of A/Wyoming viral RNA and cloned into IRES and non-IRES replicons using the primers described below.

| Primer name | Primer sequence | Utility |
|---|---|---|
| Panama HA fp pacl | CC<u>TTAATTAA</u>ATGAAGACTATCATTGC (SEQ ID NO: 1) | These primers were used to PCR amplify and clone mIL-12 into two non-IRES containing replicons, pERK and pERK-3 using the EcoRV and AscI restriction sites. |
| Panama HA rp ascl | TT<u>GGCGCGCC</u>TCAAATGCAAATGTTG (SEQ ID NO: 2) | |
| Panama HA FP Xba | CG<u>TCTAGA</u>ATGAAGACTATCATTGC (SEQ ID NO: 3) | After rtPCR, the Wy HA gene product was digested with XbaI and ligated into the IRES containing pcDNA3.3/EV71-MS which had been digested with XbaI and SAP treated. The resulting construct was then digested with AscI, to release the MS IRES/IL-12 segment which was then cloned into six different pERK plasmids containing different length stuffers: 257, 342, 357, 383, 579 and 749. (The reason the Panama HA FP Xba was used was because the |
| wyomingHArevxba | TAA AA<u>TCTAGA</u>TTAAATGCAAATGTTGCACC (SEQ ID NO: 4) | |

| Primer name | Primer sequence | Utility |
|---|---|---|
| | | sequences are identical between Panama and Wyoming at the 5' (and 3') end, so the Panama primer on hand was used for this reaction.) |
| | Restriction sites are under-lined. | |

A/Wyoming/3/2003 cODING Sequence (SEQ ID NO:5) Generated from Viral RNA by rtPCR

```
atgaagactatcattgctttaagctacattctatgcctggttttctctcaaaagcttcccggaaatgacaacagcacggca
acgctgtgccttgggcaccatgcagtaccaaacggaacgatagtgaaaacaatcacgaatgaccaaattgaagtta
ctaatgctactgagctggttcagagttcctcaacaggtggaatatgcgacagtcctcatcagatccttgatggagaaaa
ctgcacactaatagatgctctattgggagaccctcagtgtgatggcttccaaaataagaaatgggaccttttgttgagc
gcagcaaagcctacagcaactgttacccttatgatgtgccggattatgcctcccttaggtcactagttgcctcatccggc
acactggagtttaacaatgaaagcttcaattgggctggagtcactcagaatggaacaagctctgcttgcaaaaggag
atctaataaaagtttctttagtagattgaattggttgacccacttaaaatacaaatacccagcattgaacgtgactatgcc
aaacaatgaaaaatttgacaaattgtacatttgggggttcaccacccggttacggacagtgaccaaatcagcctata
tgctcaagcatcaggaagaatcacagtctctaccaaaagaagccaacaaactgtaatcccgaatatcggatataga
cccagggtaagggatatctccagcagaataagcatctattggacaatagtaaaaccgggagacatacttttgattaac
agcacaggaaatctaattgctcctcggggttacttcaaaatacgaagtgggaaaagctcaataatgagatcagatgc
acccattggcaaatgcaattctgaatgcatcactccaaatggaagcattcccaatgacaaaccatttcaaaatgtaaa
caggatcacatatgggcctgtcccagatatgttaagcaaaacactctgaaattggcaacagggatgcgaaatgtac
cagagaaacaaactagaggcatatttggcgcaatcgcgggtttcatagaaaatggttgggagggaatggtggacgg
ttggtacggtttcaggcatcaaaattctgagggcacaggacaagcagcagatctcaaaagcactcaagcagcaatc
aaccaaatcaatgggaaactgaataggttaatcgggaaaacaaacgagaaattccatcagattgaaaaagaattct
cagaagtagaagggagaattcaggacctcgagaaatatgttgaggacactaaaatagatctctggtcatacaacgc
ggagcttcttgttgccctggaaaaccaacatacaattgatctaactgactcagaaatgaacaaactgtttgaaagacc
aaagaagcaactgagggaaaatgctgaggatatgggcaatggttgtttcaaaatataccacaaatgtgacaatgcct
gcatagagtcaatcagaaatggaacttatgaccatgatgtatacagagatgaagcattaaacaaccggttccagatc
aaaggtgttgagctgaagtcaggatacaaagattggatcctatggatttcctttgccatatcatgttttttgctttgtgttgcttt
gttggggttcatcatgtgggcctgccaaaaaggcaacattaggtgcaacatttgcatttaa
```

The optimal dose combination of matched VRP and inactivated influenza vaccine can be used in conjunction with an additional adjuvant VRP strategy using VRP expressing cytokines.

Figure 4:
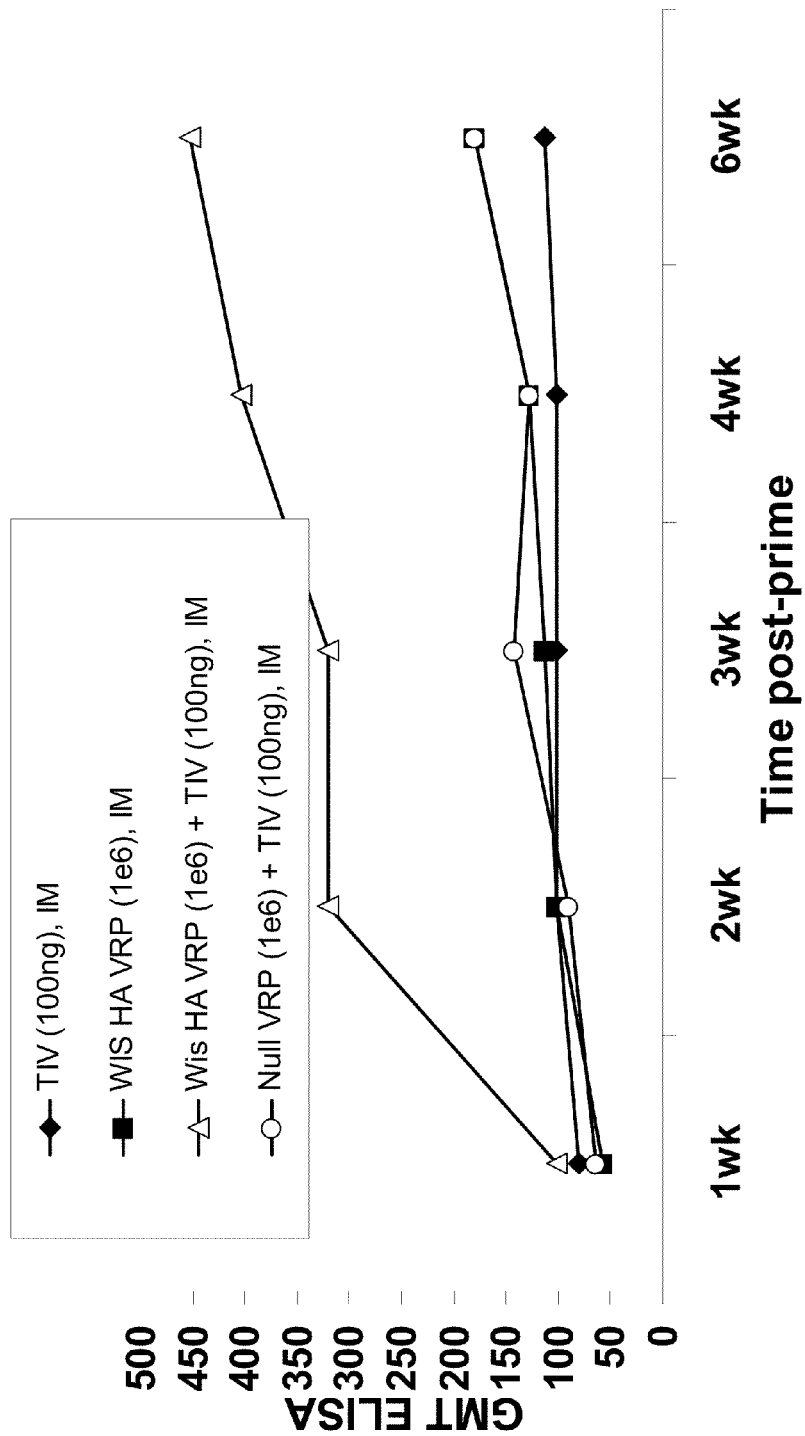
FIG. 4 shows the kinetics of the humoral response after a single dose of the indicated vaccine preparations. Seven (7) mice per group were immunized intramuscularly with a single dose of the vaccine preparation/dose indicated. Humoral responses were measured by an EL ISA assay using the H3 Wyoming protein, which cross-reacts with the HA/Wisconsin protein. Differences between the "Wisconsin HA VRP+TIV (100 ng)" data points at 4 and 6 weeks after immunization and the other immunizations are statistically significant.

In mice, a single injection of a combination of Wyoming HA recombinant protein and VRP expressing Wyoming HA induced robust immune responses using only 100 ng of recombinant protein and 5×10⁵ IU of VRP vaccine. In contrast, VRP expressing the heterologous H5 HA protein were not able to adjuvant H3-specific responses. Studies using the TIV Vaccine and a VRP vaccine expressing the HA gene from A/Wisconsin, the H3N2 strain included in the TIV vaccine, were conducted and the results are shown in FIG. 4. At the relatively low TIV dose of 100 ng, the addition of VRP expressing the H3 HA component of TIV resulted in sus- tained humoral responses (as measured by ELISA) after a single immunization. While not wishing to be bound by theory, it is likely that the titers seen at 1 week post-injection probably consists mainly of short-lived IgM. HI titers are also measured, and measurements are made at longer time periods after the single injection.

It is observed that the synergistic effects are obtained when the preformed, recombinant HA protein is homologous to the HA gene expressed from the replicon vector. The degree of genetic and antigenic homology required for this adjuvant effect is assessed by immunizing mice with VRP expressing the HA gene of A/Panama (H3N2), N Wyoming (H3N2), A/Wisconsin (H3N2), or A/New Caledonia (H1N1), each formulated individually with one of the four homologous recombinant proteins in a 4×4 matrix. ELISA and HI titers are measured to monitor the adjuvant effect on both whole protein and binding-specific epitopes. A similar assessment is carried out in the context of the combined VRP and TIV vaccine by monitoring the extent of adjuvanted responses to the homologous A/Wisconsin compared to the heterologous N New Caledonia vaccine component.

TABLE 1

Optimization of dose-activity of matched HA VRP for TIV

| | | A/Wisconsin HA VRP Adjuvant (I.U.) | | | | |
|---|---|---|---|---|---|---|
| Influenza vaccine | 0 | $10^3$ | $10^4$ | $10^5$ | $10^6$ | $10^7$ |
| TIV 100 ng | 12 | 12 | 12 | 12 | 12 | 12 |
| 10 ng | 12 | 12 | 12 | 12 | 12 | |
| | | | | | Total of 13 groups | 156 |

Groups of 12 BALB/c mice are immunized with 10 ng or 100 ng of TIV combined with and without Wisconsin HA VRP at escalating doses ranging from $10^3$ to $10^7$. Humoral and cellular responses are analyzed after each immunization as described above.

TABLE 2

Evaluation of genetic/antigenic homology required for matched HA VRP adjuvant effect

| | Recombinant HA protein | Influenza A/HA VRP adjuvant: H3 A/Panama HA VRP | H3 A/Wyoming HA VRP | H3 A/Wisconsin HA VRP | H1 A/New Caledonia HA VRP | No VRP adjuvant |
|---|---|---|---|---|---|---|
| H3 | A/Panama HA | 12 | 12 | 12 | 12 | 12 |
| | A/Wyoming HA | 12 | 12 | 12 | 12 | 12 |
| | A/WisconsinHA | 12 | 12 | 12 | 12 | 12 |
| H1 | A/New Caledonia HA | 12 | 12 | 12 | 12 | 12 |
| | No protein | 12 | 12 | 12 | 12 | 12 |
| | | | | Total of 25 groups | | 300 |

Groups of 12 BALB/c mice are immunized with VRP expressing the HA gene of A/Panama (H3N2), A/Wyoming (H3N2), A/Wisconsin (H3N2), or A/New Caledonia (H1N1), each formulated individually with one of the four homologous recombinant proteins in a 4 × 4 matrix. As controls, each of the HA VRP and HA recombinant proteins are given alone. Humoral and cellular responses are analyzed after each immunization as described above.

2006-2007 TIV products are available (Fluarix, GlaxoSmithKline; Fluzone, Sanofi; and Fluvirin, Chiron. TIV (100, 500 and 1000 ng equivalents) is mixed with VRP (e.g. 1e5, 1e6, 5e6 IU) and VRP infectivity is monitored using permissive Vero cells.

It is believed that recombinant protein preparations purchased for use in experiments described herein contained conventional adjuvanting compounds.

In some constructs, control of nucleic acid expression at the level of translation is accomplished by introducing an internal ribosome entry site (IRES) downstream of the promoter, e.g. the alphavirus 26S subgenomic promoter, and upstream of the coding sequence, e.g. for the heterologous sequence or an alphavirus structural protein, to be translated. The IRES element is positioned so that it directs translation of the mRNA, thereby minimizing, limiting or preventing initiation of translation of the mRNA from the methyl-7-guanosine (5')pppN structure present at the 5' end of the subgenomic mRNA (the "cap"). These constructs result in the IRES controlling translation of a heterologous sequence independently of promoter-driven transcription. IRESes from many different sources can be employed, including viral IRES elements from picornaviruses, e.g., poliovirus (PV) or the human enterovirus 71, e.g. strains 7423/MS/87 and BrCr thereof; from encephalomyocarditis virus (EMCV); from foot-and-mouth disease virus (FMDV); from flaviviruses, e.g., hepatitis C virus (HCV); from pestiviruses, e.g., classical swine fever virus (CSFV); from retroviruses, e.g., murine leukemia virus (MLV); from lentiviruses, e.g., simian immunodeficiency virus (SIV); from cellular mRNA IRES elements such as those from translation initiation factors, e.g., eIF4G or DAPS; from transcription factors, e.g., c-Myc or NF-κB-repressing factor (NRF); from growth factors, e.g., vascular endothelial growth factor (VEGF), fibroblast growth factor (FGF-2) and platelet-derived growth factor B (PDGF B); from homeotic genes, e.g., Antennapedia; from survival proteins, e.g., X-linked inhibitor of apoptosis (XIAP) or Apaf-1; from chaperones, e.g., immunoglobulin heavy-chain binding protein BiP, plant viruses, as well as any other IRES elements now known or later.

The following discussion and definitions are provided to improve the clarity of the present disclosure to one of ordinary skill in the relevant art.

In the context of the present application, nm means nanometer, mL means milliliter, VEE means Venezuelan Equine Encephalitis Virus, EMC means Encephalomyocarditis Virus, BHK means baby hamster kidney cells, HA means hemagglutinin gene, GFP means green fluorescent protein gene, N means nucleocapsid, FACS means fluorescence activated cell sorter, IRES means internal ribosome entry site, pfu means plaque forming units, iu means infectious units, and FBS means Fetal Bovine Serum. The expression "E2 amino acid (e.g., Lys, Thr, etc.) number" indicates designated amino acid at the designated residue of the E2 protein, and is also used to refer to amino acids at specific residues in the E3 or E1 proteins.

As used herein, the term "alphavirus" has its conventional meaning in the art, and includes the various species such as VEE Virus, Semliki Forest Virus (SFV), Sindbis, Ross River Virus, Western Equine Encephalitis Virus, Eastern Equine Encephalitis Virus, Chikungunya Virus, S.A. AR86, Everglades Virus, Mucambo Virus, Barmah Forest Virus, Middleburg Virus, Pixuna Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus, Fort Morgan Virus, Ndumu Virus, and Buggy Creek Virus. The preferred alphaviruses used in the constructs and methods are VEE, S.A. AR86, Sindbis (e.g. TR339, see U.S. Pat. No. 6,008,035), and SFV.

The terms "5' alphavirus replication recognition sequence" and "3' alphavirus replication recognition sequence" refer to the sequences found in alphaviruses, or sequences derived therefrom, that are recognized by the nonstructural alphavirus replicase proteins and lead to replication of viral RNA. These are sometimes referred to as the 5' and 3' ends, or alphavirus 5' and 3' sequences. The use of these 5' and 3' ends results in replication of the RNA sequence encoded between the two ends. The 3' alphavirus replication recognition sequence as found in the alphavirus is typically approximately 300 nucleotides in length, which contains a better defined, minimal 3' replication recognition sequence. The minimal 3' replication recognition sequence, conserved among alphaviruses, is a 19 nucleotide sequence (Hill et al. 1997. J. Virology 71: 2693-2704, 1997). These sequences can be modified by standard molecular biological techniques to further minimize the potential for recombination or to introduce cloning sites, with the proviso that they must be recognized by the alphavirus replication machinery.

The term "minimal 5' alphavirus replication recognition sequence" refers to the minimal sequence that allows recognition by the nonstructural proteins of the alphavirus but does not result in significant packaging/recombination of RNA molecules containing the sequence. Packaging/recombination of helpers can be assessed by several methods, e.g. the method described by Lu and Silver. 2001. J. Virol. Methods 91(1): 59-65).

The terms "alphavirus RNA replicon", "alphavirus replicon RNA", "alphavirus RNA vector replicon", and "vector replicon RNA" are used interchangeably to refer to an RNA molecule expressing nonstructural protein genes such that it can direct its own replication (amplification) and comprises, at a minimum, 5' and 3' alphavirus replication recognition sequences (which may be the minimal sequences, as defined above, but may alternatively be the entire regions from the alphavirus), coding sequences for alphavirus nonstructural proteins, and a polyadenylation tract. It may additionally contain one or more elements to direct the expression, meaning together and/or separately transcription and translation, of a heterologous RNA sequence. It may also be engineered to express alphavirus structural proteins. Johnston et al., Polo et al. (as cited in the background), Smith et al (International Patent Publication WO 2004/085660) and Smith et al. (U.S. Pat. No. 7,045,335) describe numerous constructs for such alphavirus RNA replicons, and such constructs are incorporated herein by reference. Specific embodiments of the alphavirus RNA replicons may contain one or more attenuating mutations, an attenuating mutation being a nucleotide deletion, addition, or substitution of one or more nucleotide(s), or a mutation that comprises rearrangement or chimeric construction which results in a loss of virulence in a live virus containing the mutation as compared to the appropriate wild-type alphavirus. Examples of an attenuating nucleotide substitution (resulting in an amino acid change in the replicon) include a mutation at nsP1 amino acid position 538, nsP2 amino acid position 96, or nsP2 amino acid position 372 in the alphavirus S.A.AR86, and an example of an attenuating mutation in the non-coding region of the replicon nucleic acid is the substitution of A or C at nucleotide 3 in VEE.

The terms "alphavirus structural protein/protein(s)" refers to one or a combination of the structural proteins encoded by alphaviruses. These are produced by the virus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2. Attenuating mutations can be introduced into any one or more of the alphavirus structural proteins.

The term "helper(s)" or "helper construct(s)" refer to a nucleic acid molecule that is capable of expressing one or more alphavirus structural proteins. Johnston et al., Polo et al. (as cited in the background), Smith et al (International Patent Publication WO 2004/085660) and Smith et al. (U.S. Pat. No. 7,045,335) describe numerous helper constructs useful for expressing alphavirus structural proteins in the production of ARPs.

The terms "helper cell" and "packaging cell" are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive, i.e. cells that are capable of producing alphavirus particles upon introduction of a viral RNA transcript. Alphavirus-permissive cells include, but are not limited to, Vero, baby hamster kidney (BHK), 293, 293T, chicken embryo fibroblast (CEF), and Chinese hamster ovary (CHO) cells. The nucleic acids encoding alphavirus structural proteins can be present in the helper cell transiently or by stable integration into the genome of the helper cell. The nucleic acid(s) encoding the alphavirus structural proteins which are used to produce alphavirus particles can be under the control of constitutive and/or inducible promoters. In one embodiment, the alphavirus structural protein coding sequences can be provided on a single DNA helper (see U.S. Pat. No. 7,045,335). Alternatively, the helper function can be provided through two helper constructs comprising an IRES element in which the translation of these coding sequences can be controlled by the activity of an IRES element. In such embodiments, the IRES element can be active in the specific helper cell type and not active, or minimally active in other cell types. In particular embodiments, the helper cells comprise nucleic acid sequences encoding the alphavirus structural proteins in a combination and/or amount sufficient to produce alphavirus particles as described herein when a recombinant replicon nucleic acid is introduced into the cell under conditions whereby the alphavirus structural proteins are produced and the recombinant replicon nucleic acid is packaged into alphavirus particles.

The terms "alphavirus replicon particles", "virus replicon particles" or "recombinant alphavirus particles", used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. Preferably, the alphavirus replicon RNA is surrounded by a nucleocapsid structure comprised of the alphavirus capsid protein, and the alphavirus glycoproteins are embedded in the cell-derived lipid envelope. The structural proteins and replicon RNA may be derived from the same or different alphaviruses. In a specific embodiment, the replicon RNA and structural proteins are based on an attenuated VEE strain, e.g. see Smith et al., U.S. Patent Publication 2005-0266550. In another specific embodiment, the replicon RNA is derived from VEE and the structural proteins are derived from Sindbis Virus (see, e.g. Dubensky et al., U.S. Pat. No. 6,376,236). The alphavirus replicon particles are infectious but propagation-defective, i.e. the replicon RNA cannot propagate beyond the host cell into which the particles initially infect, in the absence of the helper nucleic acid(s) encoding the alphavirus structural proteins.

A promoter for directing transcription of RNA from DNA, i.e. a DNA dependent RNA polymerase, is employed to produce the alphavirus replicon and helper nucleic acids. In the present context, a promoter is a sequence of nucleotides recognized by a polymerase and sufficient to cause transcription of an associated (downstream) sequence. In some embodiments, the promoter is constitutive (see below). Alternatively, the promoter may be regulated, i.e., not constitutively acting to cause transcription of the associated sequence. If inducible, there are sequences present which mediate regulation of expression so that the associated sequence is transcribed only when (i) an inducer molecule is present in the medium in or on which the cells are cultivated, or (ii) conditions to which the cells are exposed are changed to be inducing conditions. In the present context, a transcription regulatory sequence includes a promoter sequence and can further include cis-active sequences for regulated expression of an associated sequence in response to environmental signals.

In certain embodiments of the replicon and helper RNAs, transcription and translation are controlled separately by different regulatory elements. The replicon contains a promoter that directs transcription; an IRES element; and a coding sequence (e.g. for a heterologous immunogenic protein or fragment), in which the IRES element is operably located such that translation of the coding sequence is via a cap-independent mechanism directed by the IRES element and not via a cap-dependent mechanism. The term "transcription" as used herein includes the production of RNA from an alphavirus subgenomic promoter of a recombinant replicon nucleic acid, which can itself be an RNA molecule. That is, the subgenomic promoter on a recombinant replicon or helper RNA molecule can direct the transcription of a messenger RNA encoding a heterologous nucleic acid of interest or an alphavirus structural protein. Separately, the recombinant replicon or helper nucleic acid can be "replicated," i.e., copied from the 5' replication recognition sequence through to the replication recognition sequence.

In the RNA helper embodiments and to produce the replicon RNA, a promoter is utilized to synthesize RNA in an in vitro transcription reaction, and specific promoters suitable for this use include the SP6, T7, and T3 RNA polymerase promoters. In the DNA helper embodiments, the promoter functions within a cell to direct transcription of RNA. Potential promoters for in vivo transcription of the construct include eukaryotic promoters such as RNA polymerase II promoters, RNA polymerase III promoters, or viral promoters such as MMTV and MoSV LTR, SV40 early region, RSV or CMV. Many other suitable mammalian and viral promoters are available in the art. Alternatively, DNA dependent RNA polymerase promoters from bacteria or bacteriophage, e.g. SP6, T7, and T3, may be employed for use in vivo, with the matching RNA polymerase being provided to the cell, either via a separate plasmid, RNA vector, or viral vector. In a specific embodiment, the matching RNA polymerase can be stably transformed into a helper cell line under the control of an inducible promoter.

DNA constructs that function within a cell can function as autonomous plasmids transfected into the cell or they can be stably transformed into the genome. In these embodiments, the promoter may be a constitutive promoter, i.e. a promoter which, when introduced into a cell and operably linked to a downstream sequence, directs transcription of the downstream sequence upon introduction into the cell, without the need for the addition of inducer molecules or a change to inducing conditions. Alternatively, the promoter may be inducible, so that the cell only produces the functional messenger RNA encoded by the construct when the cell is exposed to the appropriate stimulus (inducer). When using an inducible promoter, the helper constructs are introduced into the packaging cell concomitantly with, prior to, or after exposure to the inducer, and expression of the alphavirus structural proteins occurs when both the constructs and the inducer are present. Alternatively, constructs designed to function within a cell can be introduced into the cell via a viral vector, e.g. adenovirus, poxvirus, adeno-associated virus, SV40, retrovirus, nodavirus, picornavirus, vesicular stomatitis virus, and baculoviruses with mammalian pol II promoters.

Once an RNA transcript (mRNA) encoding the helper or RNA replicon vectors is present in the helper cell (either via in vitro or in vivo approaches, as described above), it is eventually translated to produce the encoded polypeptides or proteins. In certain embodiments, the RNA vector replicon is transcribed in vitro from a DNA plasmid and then introduced into the helper cell by electroporation.

The alphavirus RNA vector replicon is designed to express one or more heterologous coding sequence(s) or functional RNA(s) of interest, also referred to herein as a heterologous RNA or heterologous sequence, which in the present context is the immunogenic protein or polypeptide coding sequence and which can be chosen from a wide variety of immunogenic sequences derived from viruses, prokaryotes or eukaryotes. Examples of such immunogenic heterologous sequences include, but are not limited to, immunogens (including native, modified or synthetic antigenic proteins, peptides, epitopes or immunogenic fragments), fusion proteins, cancer or tumor antigens, aberrant polypeptides associated with a diseased condition, i.e. Alzheimers'. ARPs expressing such immunogenic entities are used in combination with non-ARP immunogenic preparations. Such preparations can include an antigen, an immunogen or immunogenic polypeptide or peptide, a fusion protein, a fusion peptide, a cancer or tumor antigen, an aberrant polypeptide responsible for a disease, e.g. Alzheimers. Examples of such immunogenic polypeptides and peptides suitable for protecting a subject against a disease, include but are not limited to microbial, bacterial, protozoal, parasitic, and viral diseases. These immunogenic preparations can be in the form of purified protein or protein fragments extracted from the source (i.e. the virus, prokaryote or eukaryote), or they can be cloned and produced by recombinant techniques well known in the art.

Any amino acids which occur in the amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

As used herein, expression directed by a particular sequence is the transcription of an associated downstream sequence. If appropriate and desired for the associated sequence, there the term expression also encompasses translation (protein synthesis) of the transcribed or introduced RNA. Alternatively, different sequences can be used to direct transcription and translation.

Alphavirus-permissive cells are cells that, upon transfection with a complete viral RNA transcript, are capable of producing viral particles. Alphaviruses have a broad host range. Examples of suitable packaging cells include, but are not limited to, Vero cells, baby hamster kidney (BHK) cells, chicken embryo fibroblast cells, DF-1, 293, 293T, Chinese Hamster Ovary (CHO) cells, and insect cells.

The phrases "structural protein" or "alphavirus structural protein" as used herein refer to one or more of the alphaviral-encoded proteins which are required for packaging of the RNA replicon, and typically include the capsid protein, E1 glycoprotein, and E2 glycoprotein in the mature alphavirus (certain alphaviruses, such as Semliki Forest Virus, contain an additional protein, E3, in the mature coat). The term "alphavirus structural protein(s)" refers to one or a combination of the structural proteins encoded by alphaviruses. These are synthesized (from the viral genome) as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2.

As described herein, the structural proteins of the alphavirus are distributed among one or more helper nucleic acid molecules (e.g., a first helper RNA (or DNA) and a second helper RNA (or DNA). In addition, one or more structural proteins may be located on the same molecule as the replicon nucleic acid, provided that at least one structural protein is deleted from the replicon RNA such that the replicon and resulting alphavirus particle are replication defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "replication defective" as used herein is synonymous with "propagation-defective", and means that the particles produced in a given host cell cannot produce progeny particles in the host cell, due to the absence of the helper function, i.e. the alphavirus structural proteins required for packaging the replicon nucleic acid. However, the replicon nucleic acid is capable of replicating itself and being expressed within the host cell into which it has been introduced.

Methods for the economical and efficient production of high yield particles are described in U.S. Pat. No. 7,078,218, issued Jul. 18, 2006, as are specific attenuated strains and viruses useful for the expression of an antigenic protein or polypeptide of interest.

The helper cell, also referred to as a packaging cell, used to produce the infectious, replication defective alphavirus particles, must express or be capable of expressing alphavirus structural proteins sufficient to package the replicon nucleic acid. The structural proteins can be produced from a set of RNA molecules, typically two that are introduced into the helper cell concomitantly with or prior to introduction of the replicon vector. The first helper RNA includes RNA encoding at least one alphavirus structural protein but does not encode all alphavirus structural proteins. The first helper RNA may comprise RNA encoding the alphavirus E1 glycoprotein, but not encoding the alphavirus capsid protein and the alphavirus E2 glycoprotein. Alternatively, the first helper RNA may comprise RNA encoding the alphavirus E2 glycoprotein, but not encoding the alphavirus capsid protein and the alphavirus E1 glycoprotein. In a further embodiment, the first helper RNA may comprise RNA encoding the alphavirus E1 glycoprotein and the alphavirus E2 glycoprotein, but not the alphavirus capsid protein. In a fourth embodiment, the first helper RNA may comprise RNA encoding the alphavirus capsid, but none of the alphavirus glycoproteins. In a fifth embodiment, the first helper RNA may comprise RNA encoding the capsid and one of the glycoproteins, i.e. either E1 or E2, but not both.

In combination with any one of these first helper RNAs, the second helper RNA encodes at least one alphavirus structural protein not encoded by the first helper RNA. For example, where the first helper RNA encodes only the alphavirus E1 glycoprotein, the second helper RNA may encode one or both of the alphavirus capsid protein and the alphavirus E2 glycoprotein. Where the first helper RNA encodes only the alphavirus capsid protein, the second helper RNA may include RNA encoding one or both of the alphavirus glycoproteins. Where the first helper RNA encodes only the alphavirus E2 glycoprotein, the second helper RNA may encode one or both of the alphavirus capsid protein and the alphavirus E1 glycoprotein. Where the first helper RNA encodes both the capsid and alphavirus E1 glycoprotein, the second helper RNA may include RNA encoding one or both of the alphavirus capsid protein and the alphavirus E2 glycoprotein.

In all of the helper nucleic acids, it is understood that these molecules further comprise sequences necessary for expression (encompassing translation and where appropriate, transcription or replication signals) of the encoded structural protein sequences in the helper cells. Such sequences can include, for example, promoters (either viral, prokaryotic or eukaryotic, inducible or constitutive), IRES elements and 5' and 3' viral replicase recognition sequences. In the case of the helper nucleic acids expressing one or more glycoproteins, it is understood from the art that these sequences are advantageously expressed with a leader or signal sequence at the N-terminus of the structural protein coding region in the nucleic acid constructs. The leader or signal sequence can be derived from the alphavirus, for example E3 or 6k, or it can be a heterologous sequence such as a tissue plasminogen activator signal peptide or a synthetic sequence. Thus, as an example, a first helper nucleic acid may be an RNA molecule encoding capsid-E3-E1, and the second helper nucleic acid may be an RNA molecule encoding capsid-E3-E2. Alternatively, the first helper RNA can encode capsid alone, and the second helper RNA can encode E3-E2-6k-E1. Additionally, the packaging signal or "encapsidation sequence" that is present in the viral genome is not present in all of the helper nucleic acids. Preferably, the packaging signal is deleted from all of the helper nucleic acids.

These RNA helpers can be introduced into the cells in a number of ways. They can be expressed from one or more expression cassettes that have been stably transformed into the cells, thereby establishing packaging cell lines (see, for example, U.S. Pat. No. 6,242,259). Alternatively, the RNAs can be introduced as RNA or DNA molecules that can be expressed in the helper cell without integrating into the cell genome. Methods of introduction include electroporation, viral vectors (e.g. SV40, adenovirus, nodavirus, astrovirus), and lipid-mediated transfection.

An alternative to multiple helper RNAs is the use of a single DNA molecule, which encodes all the polypeptides necessary for packaging the viral replicon RNA into infective alphavirus replicon particles. The single DNA helper can be introduced into the packaging cell by any means known to the art, including but not limited to electroporation, lipid-mediated transfection (lipofection), viral vectored (e.g. adenovirus or SV-40), or calcium phosphate-mediated transfection. Preferably, the DNA is introduced via the electroporation-based methods. The DNA is typically electroporated into cells with a decrease in voltage and an increase in capacitance, as compared to that required for the uptake of RNA. In all electroporations, the value for the voltage and capacitance must be set so as to avoid destroying the ability of the packaging (host) cells to produce infective alphavirus particles. Alternatively, the helper function, in this format and under an inducible promoter, can be incorporated into the packaging cell genome prior to the introduction/expression of the RNA vector replicon, and then induced with the appropriate stimulus just prior to, concomitant with, or after the introduction of the RNA vector replicon.

One or more of the nucleic acids encoding the alphavirus structural proteins, i.e., the capsid, E1 glycoprotein and E2 glycoprotein, or the replicon construct, can contain one or more attenuating mutations. The phrases "attenuating mutation" and "attenuating amino acid," as used herein, mean a nucleotide mutation (which may or may not be in a region of the viral genome encoding polypeptides) or an amino acid coded for by a nucleotide mutation, which in the context of a live virus, result in a decreased probability of the alphavirus causing disease in its host (i.e., a loss of virulence), in accordance with standard terminology in the art, See, e.g., B. Davis, et al., Microbiology 156-158, (4th ed. 1990), whether the mutation be a substitution mutation, or an in-frame deletion or addition mutation. The phrase "attenuating mutation" excludes mutations which would be lethal to the virus, unless such a mutation is used in combination with a "restoring" mutation which renders the virus viable, albeit attenuated. Methods for identifying suitable attenuating mutations in the alphavirus genome are known in the art. Olmsted et al. (1984; Science 225:424) describes a method of identifying attenuating mutations in Sindbis virus by selecting for rapid growth in cell culture. Johnston and Smith (1988; Virology 162:437) describe the identification of attenuating mutations in VEE by applying direct selective pressure for accelerated penetration of BHK cells. Attenuating mutations in alphaviruses have been described in the art, e.g. White et al. 2001 *J. Virology* 75:3706; Kinney et al. 1989 *Virology* 70:19; Heise et al. 2000 *J. Virology* 74:4207; Bernard et al 2000 *Virology* 276:93; Smith et al 2001 *J. Virology* 75:11196; Heidner and Johnston 1994 *J. Virology* 68:8064; Klimstra et al. 1999 *J. Virology* 73:10387; Glasgow et al. 1991 *Virology* 185:741; Polo and Johnston 1990 *J. Virology* 64:4438; and Smerdou and Liljestrom 1999 *J. Virology* 73:1092.

In certain embodiments, the replicon RNA comprises at least one attenuating mutation. In other specific embodiments, the helper nucleic acid(s) include at least one attenuating mutation. In embodiments comprising two helper nucleic acid molecules, at least one molecule includes at least one attenuating mutation, or both can encode at least one attenuating mutation. Alternatively, the helper nucleic acid, or at least one of the first or second helper nucleic acids includes at least two, or multiple, attenuating mutations. Appropriate attenuating mutations depend upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threonine as E1 amino acid 253. Additional attenuating mutations include deletions or substitution mutations in the cleavage domain between E3 and E2 such that the E3/E2 polyprotein is not cleaved; this mutation in combination with the mutation at E1-253 is an exemplary attenuated strain. Similarly, mutations present in existing live vaccine strains, e.g. strain TC83 (see Kinney et al., 1989, *Virology* 170: 19-30, particularly the mutation at nucleotide 3), can also be used.

Where the alphavirus is the South African Arbovirus No. 86 (S.A. AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid position 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art.

Attenuating mutations may be introduced into the RNA by performing site-directed mutagenesis on the cDNA which encodes the RNA, in accordance with known procedures. See, Kunkel, *Proc. Natl. Acad. Sci. USA* 82:488 (1985), the disclosure of which is incorporated herein by reference in its entirety. Alternatively, mutations may be introduced into the RNA by replacement of homologous restriction fragments in the cDNA which codes for the RNA, in accordance with known procedures, or in cDNA copies using mutagenic polymerase chain reaction methods.

Methods are known for the preparation of infective, propagation-defective, highly immunogenic alphavirus replicon particles in high yields. In alphavirus replicon particles (ARPs), an alphavirus vector, herein referred to as a replicon, is engineered to contain and express one or more genes of interest, where at least one gene of interest is immunogenic. The alphavirus replicon vector can be derived from any alphavirus, such as Venezuelan Equine Encephalitis (VEE) virus, Sindbis virus, e.g. strain TR339, South African Arbovirus No. 86, and Semliki Forest virus, among others. The vector is then introduced into cells in culture that allow replication of alphaviruses and in which the structural proteins of the alphavirus are also expressed, so that the vector is packaged by the structural proteins into ARPs which are eventually released from the cell. U.S. Pat. No. 7,078,218 provides effective methods for the preparation of infective, propagation-defective, highly immunogenic alphavirus replicon particles in high yields.

It is recognized by those skilled in the art that the coding sequences may vary due to the degeneracy of the genetic code and codon usage. All synonymous sequences which code for the antigen or other polypeptide or protein of interest are included within the scope of this application.

Additionally, it is recognized by those skilled in the art that allelic variations may occur in the coding sequences which do not significantly change activity of the amino acid sequences of the peptides which those sequences encode. All such equivalent DNA sequences are included within the scope of this application and the definition of a promoter.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

Pharmaceutical formulations, such as vaccines or other immunogenic compositions, comprise an immunogenic amount of the infectious, propagation defective alphavirus replicon particles or live, attenuated particles in combination with a pharmaceutically acceptable carrier. An "immunogenic amount" is an amount of the infectious alphavirus particles which is sufficient to evoke an immune response in the subject to which the pharmaceutical formulation is administered. An amount of from about $10^4$ to about $10^9$, especially $10^6$ to $10^8$, infectious units, or ARPs per dose is believed suitable, depending upon the age and species of the subject being treated. Exemplary pharmaceutically acceptable carriers include, but are not limited to, sterile pyrogen-free water and sterile pyrogen-free physiological saline solution. Subjects which may be administered immunogenic amounts of the infectious, replication defective alphavirus particles include human and animal (e.g., dog, cat, cattle, horse, donkey, mouse, hamster, monkeys, guinea pigs, birds, eggs) subjects. Administration may be by any suitable means, such as intraperitoneal, intramuscular, intradermal, intranasal, intravaginal, intrarectal, subcutaneous or intravenous administration.

One or more immuno-potentiator molecules, such as chemokines and/or cytokines can be can be incorporated in the immunogenic compositions comprising the alphavirus replicon particles prepared as described herein. Alternatively, the immunogenic compositions can comprise alphavirus replicon particles which direct the expression or one or more chemokines and/or cytokines in the patient or animal to which the composition is administered. Exemplary chemokines and/or cytokines include, without limitation, interleukin-4, interleukin-12, gamma-interferon, granulocyte macrophage colony stimulating factor, and FLT-3 ligand. It is understood that the choice of cytokine and/or chemokine may vary according to the neoplasia, parasite or pathogen which is targeted for an immune response. Alternatively, an ARP expressing interleukin-12 could be used.

Immunogenic compositions comprising the ARPs (which direct the expression of the sequence(s) of interest when the compositions are administered to a human or animal) may be formulated by any of the means known in the art. Such compositions, especially vaccines, are typically prepared as injectables, either as liquid solutions or suspensions. Solid forms suitable for solution in, or suspension in, liquid prior to injection may also be prepared. Lyophilized preparations are also suitable.

The active immunogenic ingredients (the ARPs) are often mixed with excipients or carriers which are pharmaceutically acceptable and compatible with the active ingredient. Suitable excipients include but are not limited to sterile water, saline, dextrose, glycerol, ethanol, or the like and combinations thereof, as well as stabilizers, e.g. HSA or other suitable proteins and reducing sugars In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic product of the ARP resulting from administration of the immunogen in vaccines which are also comprised of the various adjuvants. Such additional formulations and modes of administration as are known in the art may also be used.

The immunogenic (or otherwise biologically active) ARP-containing compositions are administered in a manner compatible with the dosage formulation, and in such amount as is prophylactically and/or therapeutically effective. The quantity to be administered, which is generally in the range of about $10^4$ to about $10^9$ infectious units per mL in a dose, depends on the subject to be treated, the route by which the ARPs are administered, the immunogenicity of the expression product, the types of effector immune responses desired, and the degree of protection desired. Precise amounts of the active ingredient required to be administered may depend on the judgment of the physician, veterinarian or other health practitioner and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., weekly or at 1 to 4 months for a second dose, and if needed, a subsequent dose(s) after several months/years.

All references cited herein are hereby incorporated by reference to the extent there is no inconsistency with the present disclosure. The references cited in the present disclosure reflect the level of skill in the relevant arts.

Although the description herein contains certain specific information and examples, these should not be construed as limiting the scope of the invention as claimed but as merely providing illustrations of some of the presently preferred embodiments of the invention. For example, thus the scope of the invention should be determined by the appended claims and their equivalents, rather than by the examples given, but the invention may be further understood by the following non-limiting examples.

We claim:

1. A method of enhancing the immune response to an immunogenic protein in a subject, the method comprising administering an immunogenic protein to the subject, and simultaneously administering Venezuelan equine encephalitis (VEE) virus replicon particles expressing the immunogenic protein, wherein the immunogenic protein is an influenza virus hemagglutinin protein.

2. The method of claim 1 wherein the particles and the immunogenic protein are administered at the same location.

3. The method of claim 1 wherein the route of administration is subcutaneous, intradermal, intramuscular, intranasal, intraperitoneal, gastrointestinal, rectal, vaginal or via the respiratory mucosa.

4. The method of claim 1 wherein the dose of Venezuelan equine encephalitis (VEE) virus replicon particles is at least $1\times10^4$ infectious units, as measured by assay on alphavirus-permissive cell culture.

5. The method of claim 1 wherein the immune response is a humoral response and enhancement is at least five-fold.

6. The method of claim 1 wherein the method comprises a single simultaneous co-administration of the immunogenic protein and the Venezuelan equine encephalitis (VEE) virus alphavirus replicon particles expressing the immunogenic protein.

7. A method of reducing the dose of an immunogenic protein required to induce an immune response in a subject comprising administering the immunogenic protein and simultaneously co-administering Venezuelan equine encephalitis (VEE) virus replicon particles expressing said immunogenic protein wherein the dose of said immunogenic protein used is at least three-fold less than the dose of said immunogenic protein required to induce an equivalent level of immune response in the subject in the absence of administering the Venezuelan equine encephalitis (VEE) virus replicon particles expressing said immunogenic protein, wherein the immunogenic protein is an influenza virus hemagglutinin protein.

8. The method of claim 7 wherein the dose of Venezuelan equine encephalitis (VEE) virus replicon particles is at least $1\times10^4$ infectious units, as measured by assay on alphavirus-permissive cell cultures.

9. The method of claim 7 wherein the dose of influenza virus protein used is at least five-fold less than the dose of said influenza virus protein required to induce an equivalent level of immune response in the subject as in the absence of administering the Venezuelan equine encephalitis (VEE) virus replicon particles expressing said influenza virus protein.

10. The method of claim 7 wherein the dose of influenza virus protein used is at least fifty-fold less than the dose of said influenza virus protein required to induce an equivalent level of immune response in subject in the absence of administering the Venezuelan equine encephalitis (VEE) virus replicon particles expressing said influenza virus protein.

* * * * *